(12) United States Patent
Nakamura et al.

(10) Patent No.: US 12,409,198 B2
(45) Date of Patent: Sep. 9, 2025

(54) VACCINIA VIRUS THAT INDUCES CELL FUSION AND USE THEREOF

(71) Applicant: National University Corporation Tottori University, Tottori (JP)

(72) Inventors: Takafumi Nakamura, Yonago (JP); Nozomi Kuwano, Yonago (JP); Motomu Nakatake, Yonago (JP); Hajime Kurosaki, Yonago (JP)

(73) Assignees: National University Corporation Tottori University, Tottori (JP); Evolve Biotherapeutics Co., Ltd., Yonago (JP)

( * ) Notice: Subject to any disclaimer, the term of this patent is extended or adjusted under 35 U.S.C. 154(b) by 972 days.

(21) Appl. No.: 17/610,777

(22) PCT Filed: May 12, 2020

(86) PCT No.: PCT/JP2020/018976
§ 371 (c)(1),
(2) Date: Nov. 12, 2021

(87) PCT Pub. No.: WO2020/230785
PCT Pub. Date: Nov. 19, 2020

(65) Prior Publication Data
US 2022/0313761 A1    Oct. 6, 2022

(30) Foreign Application Priority Data
May 14, 2019 (JP) .................................. 2019-091609

(51) Int. Cl.
| | | |
|---|---|---|
| *A61K 35/768* | (2015.01) | |
| *A61K 35/76* | (2015.01) | |
| *A61K 39/12* | (2006.01) | |
| *A61K 39/285* | (2006.01) | |
| *A61K 39/395* | (2006.01) | |
| *A61P 35/00* | (2006.01) | |

(52) U.S. Cl.
CPC ........ *A61K 35/768* (2013.01); *A61K 39/3955* (2013.01); *A61P 35/00* (2018.01)

(58) Field of Classification Search
CPC ...... A61K 35/768; A61K 35/76; A61K 39/00; A61K 39/12; A61P 35/00
See application file for complete search history.

(56) References Cited

U.S. PATENT DOCUMENTS

| | | |
|---|---|---|
| 2006/0099224 A1 | 5/2006 | Kirn |
| 2013/0071430 A1 | 3/2013 | Nakamura et al. |
| 2016/0281066 A1 | 9/2016 | Nakamura |
| 2017/0143780 A1 | 5/2017 | Zitvogel et al. |
| 2017/0335345 A1 | 11/2017 | Kohara et al. |
| 2017/0340687 A1 | 11/2017 | Nakao et al. |
| 2018/0256751 A1 | 9/2018 | Kirn |
| 2019/0336549 A1 | 11/2019 | Hu et al. |
| 2020/0385758 A1 | 12/2020 | Bell et al. |

FOREIGN PATENT DOCUMENTS

| | | |
|---|---|---|
| JP | 2006506974 | 3/2006 |
| JP | 2017524693 | 8/2017 |
| JP | 2021509815 | 4/2021 |
| WO | 2011125469 | 10/2011 |
| WO | 2012142529 | 10/2012 |
| WO | 2015076422 | 5/2015 |
| WO | 2016076441 | 5/2016 |
| WO | 2017209053 A1 | 12/2017 |
| WO | 2018127053 | 7/2018 |
| WO | 2019134048 | 7/2019 |
| WO | 2019134049 | 7/2019 |

OTHER PUBLICATIONS

Office Action based on co-pending Japanese Application No. 2021-519440, pp. 1-5.
International Search Report based on International Application No. PCT/JP2020/018976, dated Aug. 11, 2020, pp. 1-3.
Sugimoto et al., "New Roles of Domestic Smallpox Vaccine", Protein, Nucleic Acid and Enzyme, vol. 48, No. 12, 2003, pp. 1693-1700.
European Search Report based on co-pending European Patent Application No. 20806805.6, dated Sep. 20, 2023, pp. 1-4.

*Primary Examiner* — Barry A Chestnut
(74) *Attorney, Agent, or Firm* — McCarter & English, LLC

(57) ABSTRACT

This invention provides a vaccinia virus that induces cell fusion between infected cells and a method for producing the same. Such vaccinia virus is deprived of the K2L gene or the HA gene or functions of the K2L gene and the HA gene and is mutated to induce cell fusion between infected cells and induce cell death.

13 Claims, 31 Drawing Sheets
Specification includes a Sequence Listing.

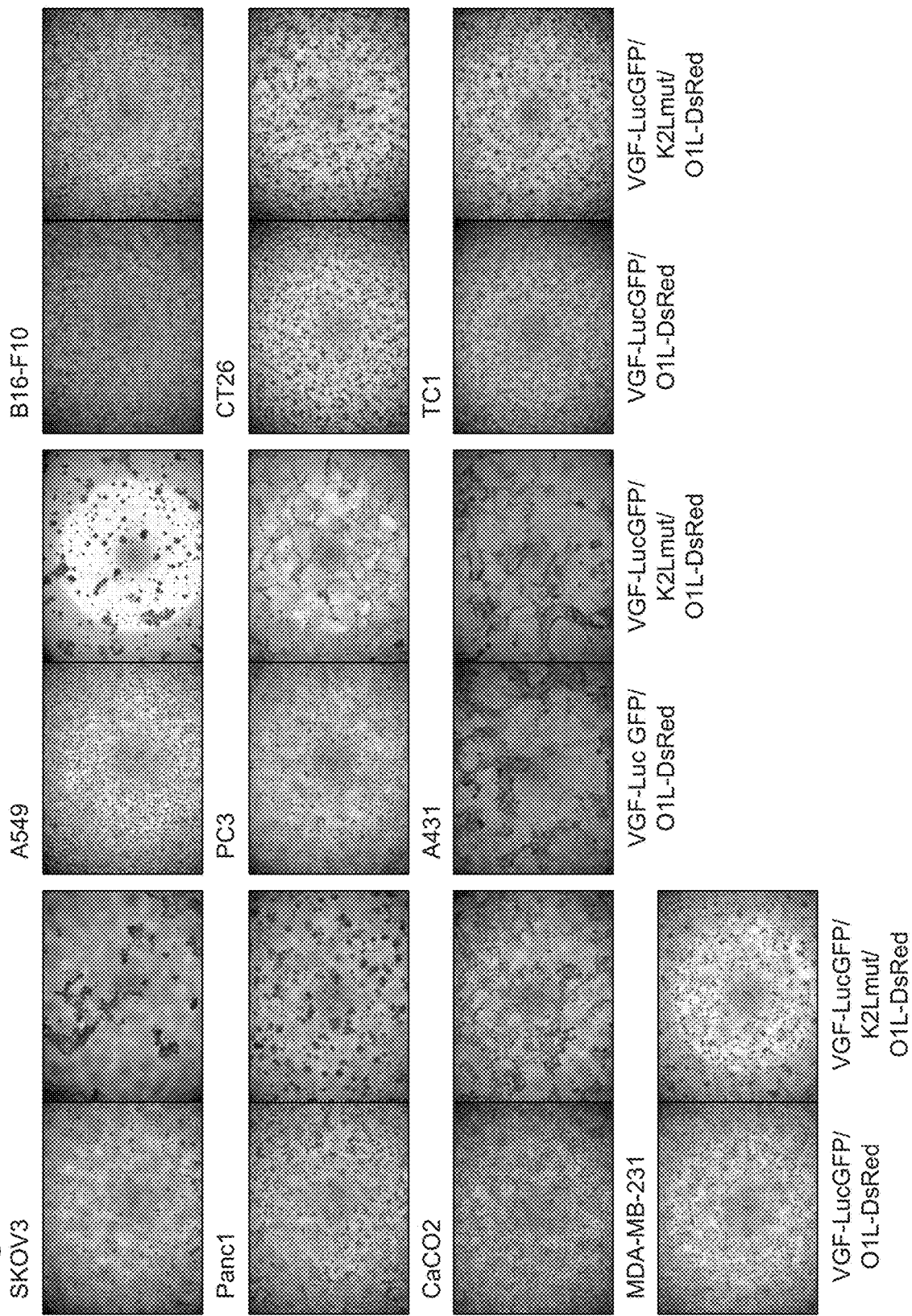

A

B

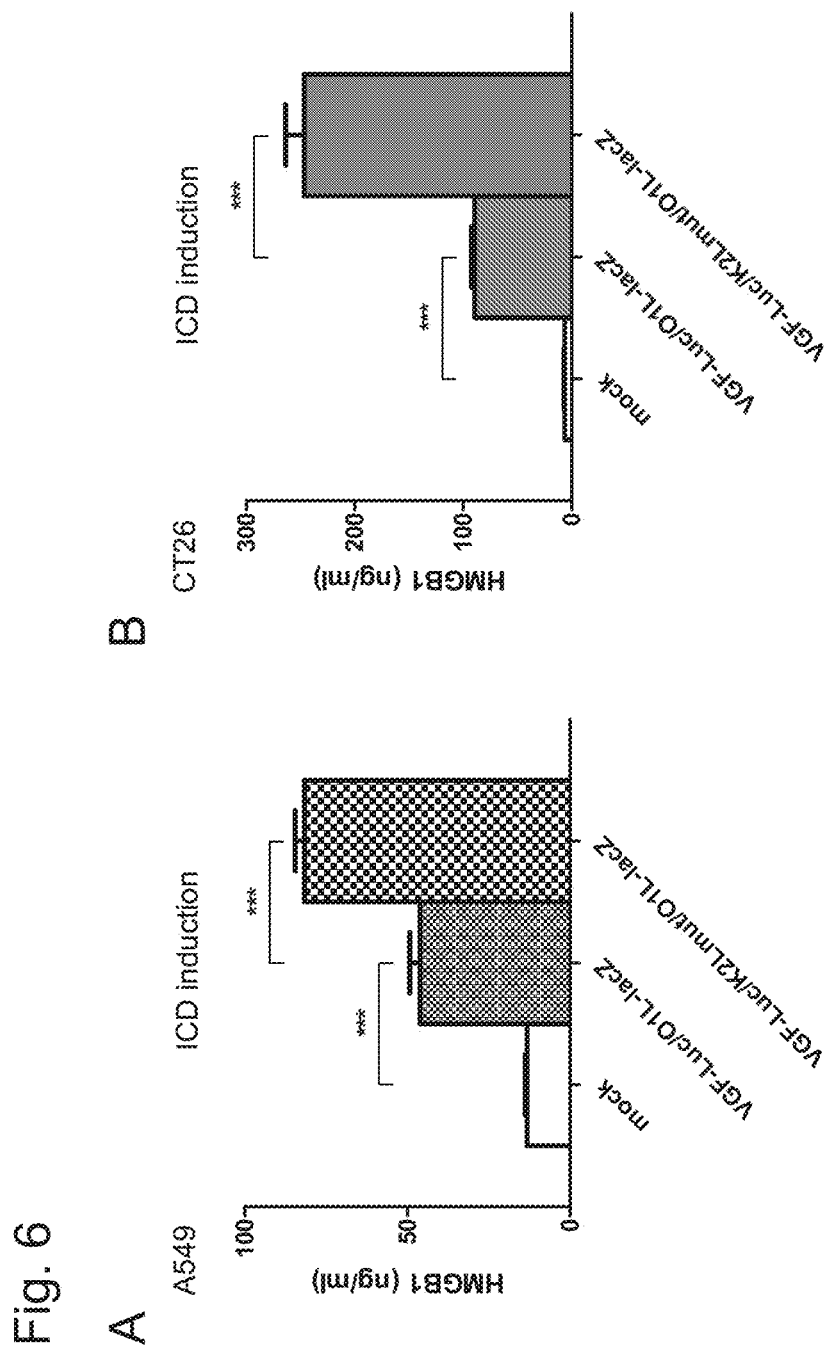

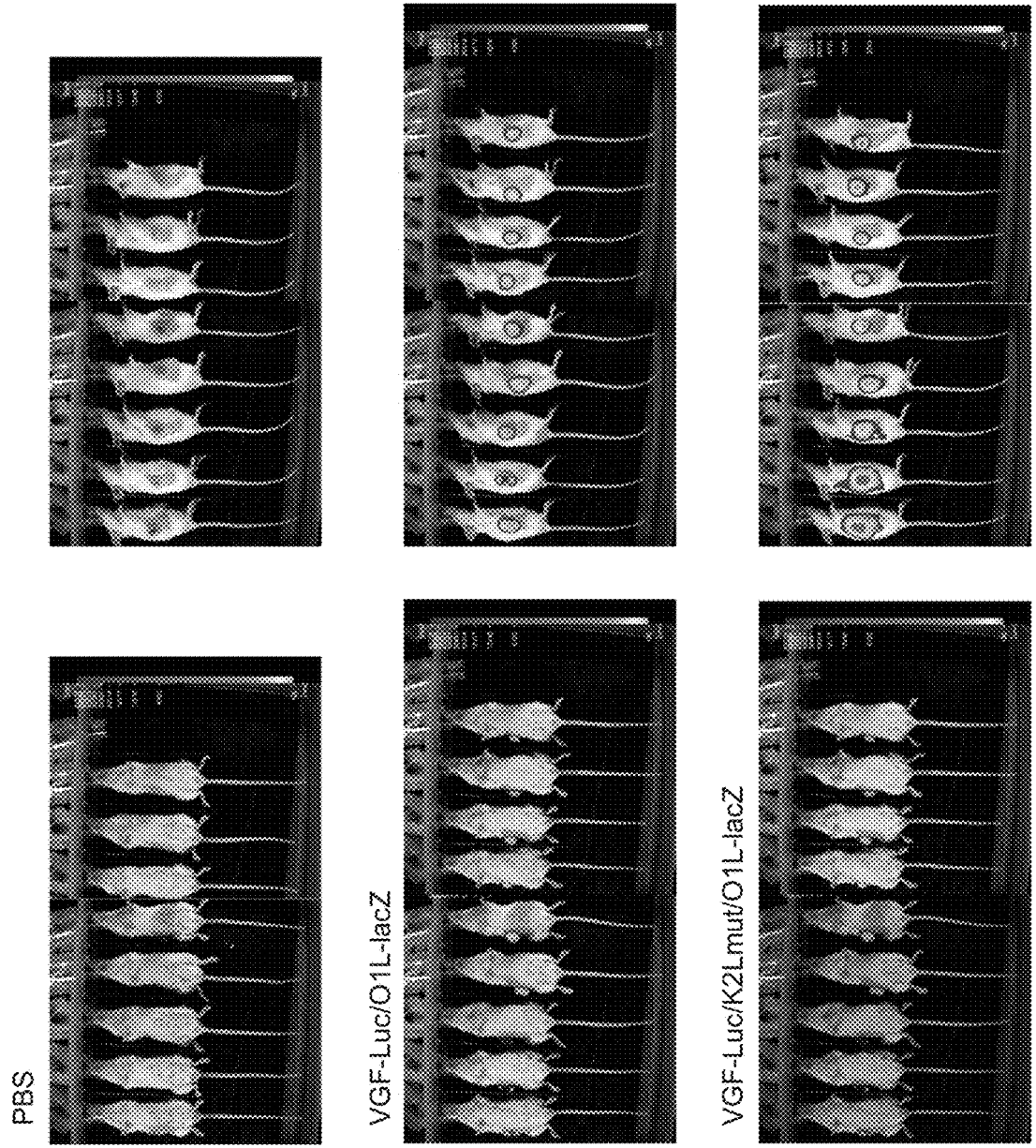

```
SEQUENCE LISTING

<160> NUMBER OF SEQ ID NOS: 21

<210> SEQ ID NO 1
<211> LENGTH: 37
<212> TYPE: DNA
<213> ORGANISM: Artificial
<220> FEATURE:
<223> OTHER INFORMATION: Primer

<400> SEQUENCE: 1
atggccggac cggccaccgg tcgccaccat gagcgag                              37

<210> SEQ ID NO 2
<211> LENGTH: 41
<212> TYPE: DNA
<213> ORGANISM: Artificial
<220> FEATURE:
<223> OTHER INFORMATION: Primer

<400> SEQUENCE: 2
tcgaattcgc tagcggccgc ttaattaagc ttgtgcccca g                        41

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
acagggatta agacggaaag                                                20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
gtcaacaagc atcttccaac                                                20

<210> SEQ ID NO 5
<211> LENGTH: 1110
<212> TYPE: DNA
```

<213> ORGANISM: Vaccinia virus

<400> SEQUENCE: 5

| | | | | | |
|---|---|---|---|---|---|
| atgattgcgt | tattgatact | atcgttagcg | tgttcagcgt | ccgcctatcg | tctacaagga | 60 |
| tttaccaatg | ccggtatagt | agcgtataaa | aatattcaag | atgataatat | tgtcttctca | 120 |
| ccgtttggtt | attcgttttc | tatgtttatg | tcgctattgc | ctgcatcagg | taatactaga | 180 |
| atagaattat | tgaagactat | ggatttgaga | aaaagagatc | tgggtccagc | atttacagaa | 240 |
| ttaatatcag | gattagctaa | gctgaaaaca | tctaaatata | cgtacactga | tctaacttat | 300 |
| caaagtttcg | tagataatac | tgtgtgtatt | aaaccgtcgt | attatcaaca | atatcataga | 360 |
| ttcggcctat | atagattaaa | ctttagacga | gatgcggtta | ataaaattaa | ttctatagta | 420 |
| gaacgtagat | ccgtatgtc | taatgtagta | gattctaata | tgctcgacaa | taatactcta | 480 |
| tgggcaatca | ttaatactat | atattttaaa | ggtatatggc | aatatccgtt | tgatatcact | 540 |
| aaaacacgca | atgctagttt | tactaataag | tacggtacga | aaacggttcc | catgatgaac | 600 |
| gtagttacta | aattgcaagg | aaatacaatc | acaatcgatg | acaaagaata | tgacatggta | 660 |
| cgccttccgt | ataaggatgc | taatattagt | atgtacctgg | caataggtga | taatatgacc | 720 |
| catttcacag | attctatcac | ggctgcaaaa | ttagactatt | gatcgtttca | attagggaat | 780 |
| aaagtgtaca | atcttaaact | ccctaaattt | tctatcgaaa | ataagaggga | tattaagtcg | 840 |
| atagccgaaa | tgatggctcc | tagtatgttt | aatccagata | atgcgtcgtt | taaacatatg | 900 |
| actagggacc | cattatatat | ttataaaatg | tttcagaatg | caaagataga | tgtcgacgaa | 960 |
| caaggaactg | tagcagaggc | atctactatt | atggtagcta | cggcgagatc | atctcctgaa | 1020 |
| aaactggaat | ttaatacacc | atttgtgttc | atcatcagac | atgatattac | tggatttata | 1080 |
| ttgtttatgg | gtaaggtgga | atctccttaa | | | | 1110 |

<210> SEQ ID NO 6
<211> LENGTH: 932
<212> TYPE: DNA
<213> ORGANISM: Vaccinia virus

<400> SEQUENCE: 6

| | | | | | |
|---|---|---|---|---|---|
| atgacacgat | taccaatact | tttgttacta | atatcattag | tatacgctac | accttctcct | 60 |
| cagacatcta | aaaataggt | gatgatgcaa | ctctatcatg | taatcgaaat | aatacaaatg | 120 |
| actacgttgt | tatgagtgct | tggtataagg | agcccaattc | cattattctt | ttagctgcta | 180 |
| aaagcgacgt | cttgtatttt | gataattata | ccaaggataa | aatatcttac | gactctccat | 240 |
| acgatgatct | agttacaact | atcacaatta | aatcattgac | tgctagagat | gccggtactt | 300 |
| atgtatgtgc | attctttatg | acatcgccta | caaatgacac | tgataaagta | gattatgaag | 360 |
| aatactccac | agagttgatt | gtaaatacag | atagtgaatc | gactatagac | ataatactat | 420 |
| ctggatctac | acattcaccg | gaaactagtt | ctgagaaacc | tgattatata | gataattcta | 480 |
| attgctcgtc | ggtattcgaa | atcgcgactc | cggaaccaat | tactgataat | gtagaagatc | 540 |
| atacagacac | cgtcacatac | actagtgata | gcattaatac | agtaagtgca | tcatctggag | 600 |
| aatccacaac | agacgagact | ccggaaccaa | ttactgataa | agaagaagat | catacagtca | 660 |
| cagacactgt | ctcatacact | acagtaagta | catcatctgg | aattgtcact | actaaatcaa | 720 |
| ccaccgatga | tacgtacaat | gataatgata | cagtaccacc | aactactgta | ggcggtagta | 780 |
| caacctctat | tagcaattat | aaaaccaagg | actttgtaga | aatatttggt | attaccgcat | 840 |
| taatttatatt | gtcggccgtg | gcaatattct | gtattacgta | ttatatatgt | aataaacgtt | 900 | cacgtaaata caaaacagag aacaaagtct ag                                    932

<210> SEQ ID NO 7
<211> LENGTH: 33
<212> TYPE: DNA
<213> ORGANISM: Artificial
<220> FEATURE:
<223> OTHER INFORMATION: Primer

<400> SEQUENCE: 7
gctccggacg ccaccatgga agatgccaaa aac                                    33

<210> SEQ ID NO 8
<211> LENGTH: 39
<212> TYPE: DNA
<213> ORGANISM: Artificial
<220> FEATURE:
<223> OTHER INFORMATION: Primer

<400> SEQUENCE: 8
gcgaattcgc tagcttacac ggcgatcttg ccgcccttc                              39

<210> SEQ ID NO 9
<211> LENGTH: 3076
<212> TYPE: DNA
<213> ORGANISM: E.coli

<400> SEQUENCE: 9
accggtcgcc accatggacc cggtggtgct gcagaggcgg gattgggaga atcctggggt        60
gacgcagctg aatcggctgg ctgctcaccc accatttgca tcatggagaa attccgaaga      120
ggcccggacc gaccgcccct ctcagcagct cagaagtctt aatggagaat ggcgcttcgc      180
atggtttcct gctcccgagg ctgtaccgga agttggctc gagtgcgatt tgcccgaggc       240
agataccgtc gtggttccct ccaactggca gatgcacggc tatgatgccc ctatctacac      300
caatgtcact taccctataa cagtgaaccc acccctttgtg cctaccgaga atcccaccgg     360
atgctacagt ctgacattta acgtggacga gtcttggctg caggaaggcc agactagaat      420
catcttcgat ggtgtcaaca cgcttttca tctgtggtgc aacgggcgtt gggtgggtta       480
cggccaagac agtaggctcc cttctgaatt cgatctctct gccttcctgc gggccggtga      540
gaatagactt gccgttatgg ttctgcgttg gagcgacggt tcctacctgg aggaccagga      600
tatgtggagg atgtctggca ttttccgaga tgtgagcctc cttcacaaac ctaccactca      660
aatctccgac tttcatgttg ccacaaggtt caacgcgacg ttttcacgcg ctgttctgga      720
ggccgaggtc caaatgtgcg gcgaactgcg cgattatctg cgcgtgactg tgagcctttg      780
gcaaggagag acacaggtgg catcaggcac cgcacccttc ggcggagaaa tcatcgacga      840
acggggagga tatgctgata gggttactct taggctgaat gtagaaaacc ccaagctctg      900
gtctgcagaa atacctaacc tctatcgcgc agttgtggaa ctgcacacgg cagacgggac      960
cctgattgaa gccgaagcct gtgacgtcgg cttccgtgaa gtgcgcatcg agaatgggct     1020
gctccttctt aacggtaagc cactgttgat cagaggcgtg aataggcatg agcatcatcc     1080
gctccacgga caggtgatgg atgagcagac aatggttcag gacatactct tgatgaaaca     1140
gaacaacttc aatgccgtgc gctgtagcca ctaccctaat cacccactgt ggtataccct     1200
gtgtgacagg tacggcctgt atgtcgtgga tgaggcaaac attgaaactc atggcatggt     1260
gccaatgaat cggctgacag atgaccccag atggctgccc gccatgtcag agcgtgtgac     1320

```
caggatggta cagcgggaca gaaatcaccc cagtgtcata atctggtccc ttgggaacga    1380
atcagggcat ggtgcaaacc acgatgctct gtaccgctgg attaagagcg ttgaccctag    1440
tcggccagtg cagtatgaag gtggaggcgc cgataccact gcaactgaca ttatttgccc    1500
aatgtacgct cgggtcgacg aggatcaacc gttccctgcg gtcccaaagt ggagcattaa    1560
gaaatggctg tctttgcctg agaaacacg cccgctgatt ctgtgcgaat atgcccacgc     1620
aatggggaac tccctgggcg ggtttgcaaa gtattggcag gcttttcgcc agtatccacg    1680
actgcaggga ggctttgtgt gggactgggt agatcagagc ctgatcaaat acgacgaaaa    1740
tggcaatcca tggtccgcct atggaggtga ctttggtgat accctaatg acaggcagtt     1800
ttgcatgaac ggactcgtct tgcagatcg aactccacat ccggccctga ctgaggccaa     1860
gcatcagcag caattcttcc agtttcggct gtctgggcag accattgagg tgacttccga    1920
gtacttgttt cgacacagcg acaatgagct gctgcactgg atggtggccc tcgatggcaa    1980
accactggcc tcaggagagg tgcccctgga tgtagcgccc caggggaaac agcttatcga    2040
gttgcccgaa ctgccccaac ccgagtctgc tgggcaactc tggcttaccg tgcgagtcgt    2100
tcagccaaat gccactgcct ggtccgaggc tggccacatt agcgcatggc agcagtggag    2160
actggctgag aacctcagcg ttacccttcc cgcagcctct cacgccatcc ctcacttgac    2220
cactagtgag atggacttct gtatcgagct gggcaacaaa cgctggcagt taacagaca     2280
gtcaggcttc ttgtcccaga tgtggattgg cgacaagaag cagctgttga cccctttgcg    2340
ggatcagttc acaagggcgc ctctggacaa tgacatcgga gtgagcgagg ctacacgaat    2400
agatccaaac gcgtgggtcg agaggtggaa ggcggctggg cactaccaag ctgaagcggc    2460
cctgttgcaa tgtaccgccg atacgctcgc cgatgccgtc ctcattacga cagcccacgc    2520
ttggcagcac cagggcaaaa cactgtttat ctcccgtaag acatacagaa tcgatgcag    2580
cggtcaaatg gccattacgg tagacgtgga agttgcgtca gatacacccc atcccgcgag    2640
gatcggactg aactgtcaat ggcccaagt cgcagagaga gtgaactggc tgggactcgg     2700
gcctcaggag aattatccag accggctcac agccgcttgc ttcgataggt gggaccttcc    2760
actctctgat atgtacaccc catacgtgtt cccctcagag aatggcctgc ggtgtgggac    2820
acgagaactg aactacggac cgcatcagtg gagagggac ttccagttca acatcagccg     2880
gtatagtcag cagcagctga tggaaacgtc ccatagacat ctgctgcacg ctgaggaagg    2940
gacatggctg aacattgacg ggttccacat gggaataggt ggcgatgaca gctggtcccc    3000
tagcgtaagc gccgagtttc aactgagtgc tgggagatat cattaccaac tggtctggtg    3060
ccagaaatga gctagc                                                   3076
```

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggtaacgcta tcgaaacgac                                                  20

<210> SEQ ID NO 11
<211> LENGTH: 20
<212> TYPE: DNA
<213> ORGANISM: Artificial
<220> FEATURE:
<223> OTHER INFORMATION: Primer

```
<400> SEQUENCE: 11
ttagttcgtc gagtgaacct 20

<210> SEQ ID NO 12
<211> LENGTH: 20
<212> TYPE: DNA
<213> ORGANISM: Artificial
<220> FEATURE:
<223> OTHER INFORMATION: Primer
<400> SEQUENCE: 12
caaggcacta tgaccgttga 20

<210> SEQ ID NO 13
<211> LENGTH: 20
<212> TYPE: DNA
<213> ORGANISM: Artificial
<220> FEATURE:
<223> OTHER INFORMATION: Primer
<400> SEQUENCE: 13
gcgatgagat acaaccggaa 20

<210> SEQ ID NO 14
<211> LENGTH: 2110
<212> TYPE: DNA
<213> ORGANISM: Vaccinia virus
<400> SEQUENCE: 14
cttgtcatca aattgtgaat catccagtcc actgaatagc aaaatcttta ctattttagt 60
atcttccaat gtggctgcct gatgtaatgg aaattcattc tctagaagat tttcaatgc 120
tccagcgttc aacaacgtac atactagacg cacgttatta tcagctattg cataatacaa 180
ggcactatga ccgttgatat ccgccttaaa tgcatctttg ctagagagaa agcttttcag 240
ctgcttagac ttccaagtat taattcgtga cagatccatg tctgaaacaa gacgctaatt 300
agtgtatatt ttttcatttt ttataatttt gtcatattgc accagaatta ataatatctc 360
taatagatct gattagtaga tacatggcta tcgcaaaaca acatatacac atttaataaa 420
aataatattt attaagaaaa ttcagatttc acgtacccat caatataaat aaaataatga 480
ttccttacac cgtacccata ttaaggagat tccaccttac ccataaacaa tataaatcca 540
gtaatatcat gtctgatgat gaacacaaat ggtgtattaa attccagttt ttcaggagat 600
gatctcgccg tagctaccat aatagtagat gcctctgcta cagttccttg ttcgtcgaca 660
tctatctttg cattctgaaa cattttataa atatataatg ggtccctagt catatgttta 720
aacgacgcat tatctggatt aaacatacta ggagccatca tttcggctat cgacttaata 780
tccctcttat tttcgataga aaatttaggg agtttaagat tgtacacttt attccctaat 840
tgaaacgacc aatagtctaa ttttgcagcc gtgatagaat ctgtgaaatg ggtcatatta 900
tcacctattg ccaggtacat actaatatta gcatccttat acggaaggcg taccatgtca 960
tattctttgt catcgattgt gattgtattt ccttgcaatt tagtaactac gttcatcatg 1020
ggaaccgttt tcgtaccgta cttattagta aaactagcat tgcgtgtttt agtgatatca 1080
aacggatatt gccatatacc tttaaaatat atagtattaa tgattgccca tagagtatta 1140
ttgtcgagca tattagaatc tactacatta gacataccgg atctacgttc tactatagaa 1200
ttaattttat taaccgcatc tcgtctaaag tttaatctat ataggccgaa tctatgatat 1260
```

| | |
|---|---:|
| tgttgataat acgacggttt aatacacaca gtattatcta cgaaactttg ataagttaga | 1320 |
| tcagtgtacg tatatttaga tgttttcagc ttagctaatc ctgatattaa ttctgtaaat | 1380 |
| gctggaccca gatctctttt tctcaaatcc atagtcttca ataattctat tctagtatta | 1440 |
| cctgatgcag gcaatagcga cataaacata gaaaacgaat aaccaaacgg tgagaagaca | 1500 |
| atattatcat cttgaatatt tttatacgct actataccgg cattggtaaa tccttgtaga | 1560 |
| cgataggcgg acgctgaaca cgctaacgat agtatcaata acgcaatcat gattttatgg | 1620 |
| tattaataat taaccttatt tttatgttcg gtataaaaaa attattgatg tctacacatc | 1680 |
| cttttgtaat tgacatctat atatccttt gtataatcaa ctctaatcac tttaactttt | 1740 |
| acagttttcc ctaccagttt atccctatat tcaacatatc tatccatatg catcttaaca | 1800 |
| ctctctgcca agatagcttc agagtgagga tagtcaaaaa gataaatata tagagcataa | 1860 |
| tcattctcgt atactctgcc ctttattaca tcacccgcat tgggcaacga ataacaaaat | 1920 |
| gcaagcatct tgttaacggg ctcgtaaatt gggataaaaa ttatgttttt attgtcttat | 1980 |
| atctatttta ttcaagagaa tattcaggaa tttcttttc cggttgtatc tcatcgcagt | 2040 |
| atatatcatt tgtacattgt tttatatttt ttaatagttt acaccttta gtaggactag | 2100 |
| tatcgtacaa | 2110 |

```
<210> SEQ ID NO 15
<211> LENGTH: 1702
<212> TYPE: DNA
<213> ORGANISM: Artificial
<220> FEATURE:
<223> OTHER INFORMATION: Synthetic

<400> SEQUENCE: 15
```

| | |
|---|---:|
| cttgtcatca aattgtgaat catccagtcc actgaatagc aaaatcttta ctattttagt | 60 |
| atcttccaat gtggctgcct gatgtaatgg aaattcattc tctagaagat ttttcaatgc | 120 |
| tccagcgttc aacaacgtac atactagacg cacgttatta tcagctattg cataatacaa | 180 |
| ggcactatga ccgttgatat ccgccttaaa tgcatctttg ctagagagaa agcttttcag | 240 |
| ctgcttagac ttccaagtat taattcgtga cagatccatg tctgaaacaa gacgctaatt | 300 |
| agtgtatatt ttttcatttt ttataatttt gtcatattgc accagaatta ataatatctc | 360 |
| taatagatct gattagtaga tacatggcta tcgcaaaaca acatatacac atttaataaa | 420 |
| aataatattt attaagaaaa ttcagatttc acgtacccat caatataaat aaaataatga | 480 |
| ttccttacac cgtacccata ttaattaagc ttgtgcccca gtttgctagg gaggtcgcag | 540 |
| tatctggcca ctgccacctc gtgctgctcg acgtaggtct cgttgttggc ctccttgatt | 600 |
| ctttccagtc tgtagtccac atagtagacg ccaggcatct tgaggttctt agcgggtttc | 660 |
| ttggatctat atgtggtctt gatgtttgcg atcagatggc tcccgcccac gagcttcagg | 720 |
| gccatgtcgt ttctgccttc caggccgccg tcagcggggt acagcgtctc ggtgaaggcc | 780 |
| tcccagccga gtgttttctt ctgcatcaca gggccgttgg atgtgaagtt caccccctctg | 840 |
| atcttgacgt tgtagatgag gcagccgtcc tggaggctgg tgtcctgggt agcggtcagc | 900 |
| acgcccccgt cttcgtatgt ggtgactctc tcccatgtga agccctcagg gaaggactgc | 960 |
| ttgaagaagt cggggatgcc ctgggtgtgg ttgatgaagg tcttgctgcc gtagaggaag | 1020 |
| ctagtagcca ggatgtcgaa ggcgaagggg agagggccgc cctcgaccac cttgattctc | 1080 |
| atggtctggg tgcccctcgta gggcttgcct tcgcccctcgg atgtgcactt gaagtgatgg | 1140 |
| ttgtccacgg tgccctccat gtacagcttc atgtgcatgt tctccttaat cagctcgctc | 1200 |

-continued

```
atgattttat ggtattaata attaacctta tttttatgtt cggtataaaa aaattattga   1260
tgtctacaca tccttttgta attgacatct atatatcctt ttgtataatc aactctaatc   1320
actttaactt ttacagtttt ccctaccagt ttatccctat attcaacata tctatccata   1380
tgcatcttaa cactctctgc caagatagct tcagagtgag gatagtcaaa aagataaata   1440
tatagagcat aatcattctc gtatactctg ccctttatta catcacccgc attgggcaac   1500
gaataacaaa atgcaagcat cttgttaacg ggctcgtaaa ttgggataaa aattatgttt   1560
ttattgtctt atatctattt tattcaagag aatattcagg aatttctttt tccggttgta   1620
tctcatcgca gtatatatca tttgtacatt gttttatatt ttttaatagt ttacaccttt   1680
tagtaggact agtatcgtac aa                                              1702

<210> SEQ ID NO 16
<211> LENGTH: 20
<212> TYPE: DNA
<213> ORGANISM: Artificial
<220> FEATURE:
<223> OTHER INFORMATION: Primer
<400> SEQUENCE: 16
ttaacatccg ttgatggaag                                                   20

<210> SEQ ID NO 17
<211> LENGTH: 20
<212> TYPE: DNA
<213> ORGANISM: Artificial
<220> FEATURE:
<223> OTHER INFORMATION: Primer
<400> SEQUENCE: 17
ttagtcgcca tgactatctc                                                   20

<210> SEQ ID NO 18
<211> LENGTH: 24
<212> TYPE: DNA
<213> ORGANISM: Artificial
<220> FEATURE:
<223> OTHER INFORMATION: Primer
<400> SEQUENCE: 18
atttctccgt gataggtatc gatg                                              24

<210> SEQ ID NO 19
<211> LENGTH: 22
<212> TYPE: DNA
<213> ORGANISM: Artificial
<220> FEATURE:
<223> OTHER INFORMATION: Primer
<400> SEQUENCE: 19
aacggtttac gttgaaatgt cc                                                22

<210> SEQ ID NO 20
<211> LENGTH: 1110
<212> TYPE: DNA
<213> ORGANISM: Vaccinia virus
<400> SEQUENCE: 20
atgattgcgt tattgatact atcgttagcg tgttcagcgt ccgcctatcg tctacaagga     60
tttaccaatg ccggtatagt agcgtataaa aatattcaag atgataatat tgtcttctca    120
```

```
ccgtttggtt attcgttttc tatgtttatg tcgctattgc ctgcatcagg taatactaga    180
atagaattat tgaagactat ggatttgaga aaaagagatc tgggtccagc atttacagaa    240
ttaatatcag gattagctaa gctgaaaaca tctaaatata cgtacactga tctaacttat    300
caaagtttcg tagataatac tgtgtgtatt aaaccgtcgt attatcaaca atatcataga    360
ttcggcctat atagattaaa ctttagacga gatgcggtta ataaaattaa ttctatagta    420
gaacgtagat ccggtatgtc taatgtagta gattctaata tgctcgacaa taatactcta    480
tgggcaatca ttaatactat atattttaaa ggtatatggc aatatccgtt tgatatcact    540
aaaacacgca atgctagttt tactaataag tacggtacga aaacggttcc catgatgaac    600
gtagttacta aattgcaagg aaatacaatc acaatcgatg acaaagaata tgacatggta    660
cgccttccgt ataaggatgc taatattagt atgtacctgg caataggtga taatatgacc    720
catttcacag attctatcac ggctgcaaaa ttagactatt ggtcgtttca attagggaat    780
aaagtgtaca atcttaaact ccctaaattt tctatcgaaa ataagaggga tattaagtcg    840
atagccgaaa tgatggctcc tagtatgttt aatccagata atgcgtcgtt taaacatatg    900
actagggacc cattatatat ttataaaatg tttcagaatg caaagataga tgtcgacgaa    960
caaggaactg tagcagaggc atctactatt atggtagcta cggcgagatc atctcctgaa    1020
aaactggaat ttaatacacc atttgtgttc atcatcagac atgatattac tggatttata    1080
ttgtttatgg gtaaggtgga atctccttaa                                    1110

<210> SEQ ID NO 21
<211> LENGTH: 933
<212> TYPE: DNA
<213> ORGANISM: Vaccinia virus

<400> SEQUENCE: 21
atgacacgat taccaatact tttgttacta atatcattag tatacgctac accttctcct     60
cagacatcta aaaaaatagg tgatgatgca actctatcat gtaatcgaaa taatacaaat    120
gactacgttg ttatgagtgc ttggtataag gagcccaatt ccattattct tttagctgct    180
aaaagcgacg tcttgtattt tgataattat accaaggata aaatatctta cgactctcca    240
tacgatgatc tagttacaac tatcacaatt aaatcattga ctgctagaga tgccggtact    300
tatgtatgtg cattctttat gacatcgcct acaaatgaca ctgataaagt agattatgaa    360
gaatactcca cagagttgat tgtaaataca gatagtgaat cgactataga cataatacta    420
tctggatcta cacattcacc ggaaactagt tctgagaaac ctgattatat agataaattct    480 aattgctcgt cggtattcga aatcgcgact ccggaaccaa ttactgataa tgtagaagat    540
catacagaca ccgtcacata cactagtgat agcattaata cagtaagtgc atcatctgga    600
gaatccacaa cagacgagac tccggaacca attactgata agaagaaga tcatacagtc    660 acagacactg tctcatacac tacagtaagt acatcatctg gaattgtcac tactaaatca    720
accaccgatg atacgtacaa tgataatgat acagtaccac caactactgt aggcggtagt    780
acaacctcta ttagcaatta taaaaccaag gactttgtag aaatatttgg tattaccgca    840
ttaattatat tgtcggccgt ggcaatattc tgtattacga attatatatg taataaacgt    900
tcacgtaaat acaaaacaga gaacaaagtc tag                                933
```

VACCINIA VIRUS THAT INDUCES CELL FUSION AND USE THEREOF

CROSS-REFERENCE TO RELATED APPLICATIONS

This application is a national stage application filed under 35 U.S.C. § 371 of PCT/JP2020/018976, filed May 12, 2020, which claims the benefit of Japanese Patent Application No. 2019-091609, filed May 14, 2019, all of which are incorporated herein, in their entireties, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 11924400144EQUENCELISTING.txt. The size of the text file is 18 KB, and the text file was created on Nov. 12, 2021.

TECHNICAL FIELD

The present invention relates to a vaccinia virus that induces cell fusion between infected cells.

BACKGROUND ART

Currently, preclinical studies and clinical studies on cancer therapies using live viruses have been actively conducted worldwide. The cancer virotherapy is a method utilizing inherent nature of viruses, which is to kill infected cells and tissues by growing and transmitting therein. Such a method, compared to the conventional radiation therapy and chemotherapy, exhibits anticancer effects via diverse mechanisms by oncolysis due to virus growth, followed by induction of antitumor immunity associated therewith.

There are vaccine strains of a vaccinia virus, which were established in Japan in the past, have been used in humans as a smallpox vaccine, and have proven to be highly safe (see Non-Patent Literature 1). However, the strains still retain the attenuated growth capacity in normal tissues, and, thus, it was necessary to modify the strain to grow only in cancer cells, so as to establish such strains as a means of cancer virus therapy with higher safety. Thus, such vaccine strains were modified by a gene recombination technique, and a gene recombinant vaccinia virus specifically growing in and damaging cancer cells was successfully developed using control dysfunction of the MAPK/ERK pathway in a wide range of cancers as the indicator (see Patent Literatures 1 and 2).

CITATION LIST

Patent Literature

Patent Literature 1: WO 2011/125469
Patent Literature 2: WO 2015/076422

Non-Patent Literature

Non-Patent Literature 1: PROTEIN, NUCLEIC ACID AND ENZYME, Vol. 48, No. 12, 2003, pp. 1693-1700

SUMMARY OF INVENTION

Technical Problem

The present invention provides a vaccinia virus that induces cell fusion between infected cells and a method for producing the same.

Solution to Problem

The present inventors have conducted studies concerning antitumor effects of vaccinia viruses. As a result, they discovered that deletion of the K2L gene or HA gene of vaccinia viruses would induce cell fusion between infected cells and then cause cell death. Specifically, vaccinia viruses deprived of the K2L gene or HA gene exerted anticancer effects by infecting cancer cells. In addition, they discovered that synergistic anticancer effects would be exerted by deleting the K2L gene or HA gene from oncolytic vaccinia viruses. This has led to the completion of the present invention.

Specifically, the present invention is as follows.

[1] A vaccinia virus mutated to induce cell fusion between infected cells.
[2] The vaccinia virus according to [1], which is deprived of functions of the K2L gene or the HA gene, or functions of the K2L gene and the HA gene, induces cell fusion between infected cells, and induces cell death.
[3] The vaccinia virus according to [1] or [2], which is an oncolytic vaccinia virus.
[4] The vaccinia virus according to [3], which has oncolytic effects of not growing in normal cells, growing specifically in cancer cells, and specifically damaging cancer cells.
[5] The vaccinia virus according to any of [1] to [4], wherein the vaccinia virus is LC16 strain, LC16mO strain, or LC16m8 strain modified to express the B5R gene therein.
[6] A pharmaceutical composition used for cancer therapy comprising the vaccinia virus according to any of [1] to [5].
[7] A vaccinia virus vector comprising foreign DNA introduced into the vaccinia virus according to any of [1] to [5].
[8] The vaccinia virus vector according to [7], wherein the foreign DNA is marker DNA, a therapeutic gene having cytotoxic or immunostimulatory effects, or DNA encoding an antigen of a cancer, a virus, a bacterium, or a protozoan.
[9] A pharmaceutical composition used for cancer therapy or used as a vaccine against a cancer, a virus, a bacterium, or a protozoan, which comprises the vaccinia virus vector according to [7] or [8].
[10] A method for producing a vaccinia virus that induces cell fusion between infected cells to induce cell death, comprising deleting functions of the K2L gene or the HA gene, or functions of the K2L gene and the HA gene from the vaccinia virus.
[11] The method of production according to [10], wherein the vaccinia virus is an oncolytic vaccinia virus.
[12] The method of production according to [10] or [11], which further comprises deleting functions of the vaccinia virus growth factor (VGF) gene or O1L gene, or functions of the vaccinia virus growth factor (VGF) gene and O1L gene.
[13] The method of production according to any of [10] to [12], wherein the vaccinia virus is LC16 strain, LC16mO strain, or LC16m8 strain modified to express the B5R gene therein.

[14] A combination pharmaceutical kit used for cancer therapy, which comprises the vaccinia virus according to any of [1] to [5] in combination with an immune checkpoint inhibitor.

[15] The combination pharmaceutical kit according to [14], wherein the immune checkpoint inhibitor is anti-PD-1 antibody or anti-PD-L1 antibody.

[16] The vaccinia virus according to any of [1] to [5], which is used for cancer therapy in combination with the immune checkpoint inhibitor.

[17] The vaccinia virus according to [16], wherein the immune checkpoint inhibitor is anti-PD-1 antibody or anti-PD-L1 antibody.

The present description includes the disclosed contents of JP Patent Application No. 2019-91609, which is the basis of the priority of the present application.

Advantageous Effects of Invention

When a vaccinia virus is deprived of a gene, such as the K2L gene or the HA gene, the vaccinia virus induces cell fusion between infected cells, and anticancer effects are then enhanced. At the outset, the growth capacity and the transmissibility of the virus are enhanced, oncolytic effects are improved, and apoptosis and necrosis then occur frequently. Subsequently, immunogenic cell death (ICD) is induced more efficiently as a result of cell fusion, and CD8 T cells frequently infiltrate the tumor on the side to which the virus has been administered (hereafter, referred to as the "virus-administered side") and the tumor on the side to which the virus has not been administered (hereafter, referred to as the "virus non-administered side"). In the end, the immune environments of the tumor on the virus-administered side and the tumor on the virus non-administered side are improved, and cancer immunity is then likely to function. Specifically, the cell fusion-inducing oncolytic viruses convert cold tumors that are less susceptible to the immune system to hot tumors that are prone to attack from the immune system. Thus, the oncolytic viruses that induce cell fusion exert higher anticancer effects than the oncolytic viruses that do not induce cell fusion.

BRIEF DESCRIPTION OF DRAWINGS

FIGS. 1A to C show structures of VGF-LucGFP/O1L-DsRed and the cell fusion-inducing gene recombinant vaccinia viruses derived therefrom. FIGS. 1D and E show structures of VGF-Luc/O1L-LacZ and the cell fusion-inducing gene recombinant vaccinia virus derived therefrom.

FIG. 3-1 shows images of cells infected with the cell fusion-inducing gene recombinant vaccinia viruses.

FIG. 3-2 shows cytotoxicity of the cell fusion-inducing gene recombinant vaccinia viruses.

FIG. 3-3 shows the amount of cell fusion-inducing gene recombinant vaccinia virus production.

FIG. 4-1 shows images of 10 types of tumor cells infected with the cell fusion-inducing gene recombinant vaccinia viruses.

FIG. 4-2 shows viability of 10 types of tumor cells infected with the cell fusion-inducing gene recombinant vaccinia viruses.

FIG. 5-1 shows cell death induced by the cell fusion-inducing gene recombinant vaccinia viruses. FIG. 5-1A shows apoptosis occurred in A549 and FIG. 5-1B shows necrosis occurred in A549.

FIG. 5-2 shows cell death induced by the cell fusion-inducing gene recombinant vaccinia viruses. FIG. 5-2A shows apoptosis occurred in CT26 and FIG. 5-2B shows necrosis occurred in CT26.

FIG. 6 shows immunogenic cell death (ICD) induced by the cell fusion-inducing gene recombinant vaccinia viruses. FIG. 6A shows ICD occurred in A549 and FIG. 6B shows ICD occurred in CT26.

FIG. 7A shows virus administration directly into the tumor on one side and FIG. 7B shows a schedule of administration and detection.

FIG. 8-1 shows the distribution of cell fusion-inducing gene recombinant vaccinia virus growth in allogeneic transplantation mouse models.

FIG. 8-2 shows the quantified cell fusion-inducing gene recombinant vaccinia virus growth in allogeneic transplantation mouse models. FIG. 8-2A shows vaccinia virus growth on the virus-administered side and FIG. 8-2B shows vaccinia virus growth on the virus non-administered side.

FIG. 9A shows the tumor volume on the virus-administered side and FIG. 9B shows the tumor volume on the virus non-administered side.

FIG. 10-1 shows the results of immunological analysis of the allogeneic transplantation mouse models after the therapy with the cell fusion-inducing gene recombinant vaccinia viruses (Part 1).

FIG. 10-2 shows the results of immunological analysis of the allogeneic transplantation mouse models after the therapy with the cell fusion-inducing gene recombinant vaccinia viruses (Part 2).

FIG. 11A shows the control results attained by administration of the isotype control and FIG. 11B shows the results attained by administration of the anti-CD8 antibody. In FIGS. 11A and 11B, the charts shown on the left show the results concerning the virus-administered side, and the charts shown on the right show the results concerning the virus non-administered side.

FIG. 12A shows virus administration directly into the tumor on one side and FIG. 12B shows a schedule of administration and detection.

FIG. 13-1 shows the distribution of cell fusion-inducing gene recombinant vaccinia virus growth in the allogeneic transplantation mouse models for advanced tumors.

FIG. 13-2 shows the quantified cell fusion-inducing gene recombinant vaccinia virus growth in the allogeneic transplantation mouse models for advanced tumors.

FIG. 15-1 shows structures of vaccinia viruses having both the ability of cell fusion and the tumor targeting ability.

FIG. 15-2 shows cell viability after infection with the vaccinia viruses having both the ability of cell fusion and the tumor targeting ability (Part 1).

FIG. 15-3 shows cell viability after infection with the vaccinia viruses having both the ability of cell fusion and the tumor targeting ability (Part 2).

FIG. 15-4 shows immunogenic cell death after infection with the vaccinia viruses having both the ability of cell fusion and the tumor targeting ability (Part 1).

FIG. 15-5 shows immunogenic cell death after infection with the vaccinia viruses having both the ability of cell fusion and the tumor targeting ability (Part 2).

FIG. 17A shows virus administration directly into the tumor on one side and FIG. 17B shows a schedule of administration and detection.

FIG. 18A shows the results when the anti-PD-1 antibody is not used and FIG. 18B shows the results when the anti-PD-1 antibody is used in combination. In FIGS. 18A and 18B, the charts shown on the left show the results concerning the virus-administered side and the charts shown on the right show the results concerning the virus non-administered side.

DESCRIPTION OF EMBODIMENTS

Figure 1:
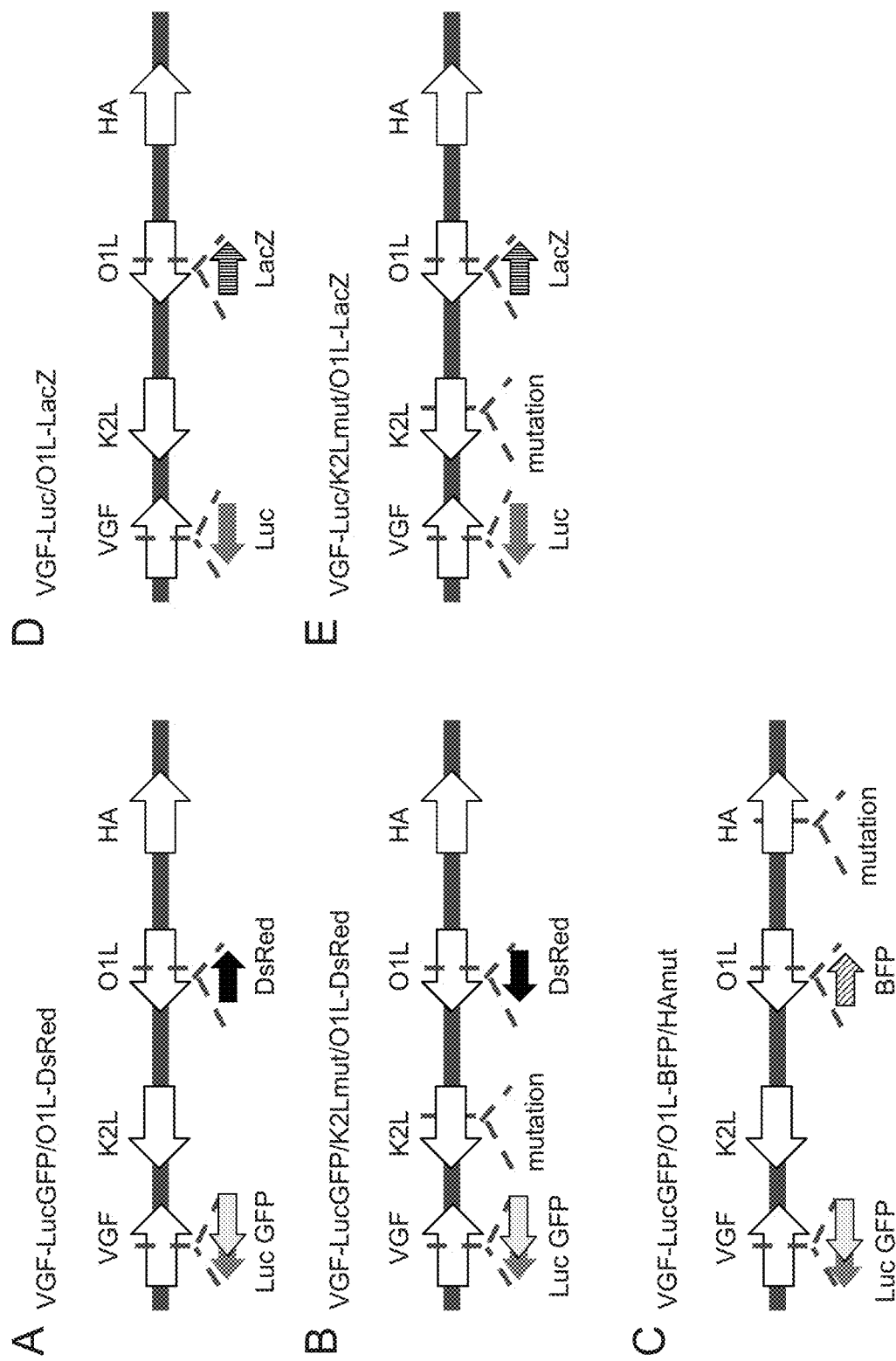
FIG. 1 shows structures of the cell fusion-inducing gene recombinant vaccinia viruses.

Hereinafter, the present invention is described in detail.

The vaccinia virus of the present invention is a vaccinia virus that is mutated to have the ability of cell fusion. When the vaccinia virus having "the ability of cell fusion" infects cells herein, the vaccinia virus can induce cell fusion between infected cells. The vaccinia virus that is mutated to have the ability of cell fusion is deprived of functions of a gene that suppresses the ability of cell fusion inherent to the vaccinia virus, or such vaccinia virus comprises a gene that promotes cell fusion inserted and expressed therein.

Concerning cell fusion, the vaccinia virus inherently comprises genes that suppress the ability of cell fusion, such as the K2L gene and the HA (A56R) gene, the vaccinia virus of the present invention is deprived of the K2L gene or the HA gene or functions of the K2L gene and the HA gene, and a phenotype of the vaccinia virus of the present invention is thus modified to have the ability of cell fusion. As demonstrated in FIG. 8 (page 5189) of Wagenaar et al., Journal of Virology, Vol. 82, No. 11, June 2008, pp. 5153-5160, a complex of the HA (A56R) protein and the K2L protein is immobilized on a cell membrane through a transmembrane domain of HA in cells infected with vaccinia viruses. The entry/fusion complex (EFC) composed of a plurality of virus proteins (A21L, A28L, G3L, H2R, J5L, and L5R) is immobilized on a mature virus membrane together with virus proteins G9R and A16L. It is considered that G9R and A16L act on HA and K2L on a cell membrane and inhibit fusion between viruses and cells infected therewith. Thus, HA and K2L are impaired to be deprived of inhibitory activity, and cell fusion can be thus induced. Accordingly, examples of genes that are associated with cell fusion and suppress the ability of cell fusion inherent to the vaccinia virus include, in addition to K2L and HA encoding virus proteins, A16L, A21L, A25L, A26L, A28L, G3L, G9R, H2R, J5L, and L5R genes. Concerning G9R, for example, H at position 44 is mutated with Y. Such mutation induces cell fusion even if a molecule that suppresses cell fusion is normal. This indicates that deletion of one or more functions thereof or introduction of a mutation would induce or accelerate cell fusion. An example of a combination is deletion of K2L and mutation of H with Y at position 44 of G9R.

Several types of virus proteins having the ability of cell fusion are known. When genes of such proteins are inserted and expressed in a virus having different oncolytic effects, the virus can be mutated to have the ability of cell fusion. Examples of such genes include genes encoding the H (hemagglutinin) protein and the F (fusion) protein derived from the measles virus. As demonstrated in the U.S. Pat. No. 7,635,752, particular cells can be induced to undergo cell fusion by modification of the H gene. It is also demonstrated that such genes may be expressed in the adenovirus or the vesicular stomatitis virus (VSV) and the resultants may be used for cancer therapy (Nakamura et al., NATURE BIOTECHNOLOGY, VOLUME 22, NUMBER 3, MARCH 2004, pp. 331-336). Another example is a gene encoding the GaLV envelope derived from the Gibbon ape leukemia virus (GaLV). It is also demonstrated that such gene may be expressed in the herpes virus, adenovirus, or lentivirus and the resultant may be used for cancer therapy (Krabee et al., Cancers 2018, 10, 216; doi: 10.3390/cancers10070216).

In addition, VSV that expresses the FAST protein derived from the reovirus, the adenovirus that expresses the HIV envelop derived from HIV, VSV that expresses the F protein derived from the Newcastle disease virus (NDV), and the adenovirus that expresses the F protein derived from SV5 have been reported (Krabee et al., Cancers 2018, 10, 216; doi: 10.3390/cancers10070216).

Specifically, examples of genes that promote cell fusion include a gene encoding the FAST protein derived from the reovirus, a gene encoding the HIV envelope derived from HIV, a gene encoding the F protein derived from NDV, and a gene encoding the F protein derived from SV5.

The K2L gene is known as a serine protease inhibitor, although functions thereof remain less known. The HA gene is a glycoprotein that is induced on the infected cell surface and it is known as the hemagglutinin. SEQ ID NO: 20 shows the nucleotide sequence of the wild-type K2L gene and SEQ ID NO: 21 shows the nucleotide sequence of the wild-type HA gene.

When the vaccinia virus is deprived of functions of the K2L gene or the HA gene, the K2L gene or the HA gene is not expressed therein. Even if the K2L gene or the HA gene is expressed, the protein expressing the K2L gene or the HA gene does not retain normal functions of the K2L protein or the HA protein. In order to delete functions of the K2L gene or the HA gene from the vaccinia virus, the entire or part of the K2L gene or the HA gene may be deleted. Alternatively, the gene may be mutated by substitution, deletion, or addition of nucleotides, so that the normal K2L protein or HA protein cannot be expressed. Alternatively, a foreign gene may be inserted into the K2L gene or the HA gene. While cell fusion is induced by deletion of K2L or HA, in the present invention, induction of cell fusion is critical for anti-cancer effects. To this end, virus genes other than K2L and HA may be deleted.

Gene functions can be deleted by known techniques, such as genome editing, homologous recombination, RNA interference, the antisense method, gene insertion, artificial mutagenesis, or PTGS involving the use of a virus vector. When a normal gene product is not expressed because of gene deletion or mutation, in the present invention, a gene of interest is deleted.

Homologous recombination is a phenomenon in which two DNA molecules are mutually recombined via the same nucleotide sequence in a cell and is the method often used for recombining viruses having an enormous genome DNA such as the vaccinia virus. First, a plasmid to which another DNA is ligated to split the K2L gene or HA gene sequence of the target vaccinia virus in the middle thereof is constructed (the resulting plasmid is referred to as a "transfer vector"). The transfer vector is then introduced into cells infected with the vaccinia virus, recombination takes place between the virus DNA that became naked during the virus replication and the same sequence of the transfer vector, the inserted DNA is incorporated into the target gene of the virus genome, and the gene is then deprived of its functions. Examples of cells that can be infected with vaccinia viruses include BSC-1 cells, HTK-143 cells, Hep2 cells, MDCK cells, Vero cells, HeLa cells, CV1 cells, COS cells, RK13 cells, BHK-21 cells, and primary rabbit kidney cells. Vectors may be introduced into cells in accordance with a conventional technique, such as the calcium phosphate method, the cationic ribosome method, or electroporation.

Genome editing is a method of using a site-specific nuclease to modify a target gene. Methods of genome editing vary depending on types of nucleases to be used, and examples thereof include the zinc finger nuclease (ZFN) method (Urnov, Fyodor D. et al., Natur., Vol. 435, 2 Jun. 2005, pp. 642-651), the Tale nuclease (TALEN) method (Mahfouz, Magdy M. et al., PNAS Feb. 8, 2011, 108 (6), pp. 2623-2628), and methods involving the use of the CRISPR/Cas systems, such as CRISPR (clustered regularly interspaced short palindromic repeats)/Cas9 (Crispr associated protein 9) (Jinek, Martin, et al., Science, Vol. 337, 17 Aug. 2012, pp. 816-821) and CRISPR/Cas3. A method of nuclease modification such as a method involving the use of nickase-modified Cas is within the scope of the methods above. The method involving the use of the CRISPR/Cas9 system is particularly preferable. According to the CRISPR/Cas9 system, a sequence of interest is cleaved with guide RNA comprising a sequence complementary to a target sequence of the gene to be deprived of its functions via cleavage (i.e., crRNA or tracrRNA) and a Cas9 nuclease. After the genome is cleaved, the sequence is repaired via non-homologous end joining (NHEJ), nucleotide deletion or the like is induced, and the gene of interest can be knocked out. After the genome is cleaved, alternatively, a target gene can be induced to mutate via homologous recombination by means of homology-directed repair (HDR). When the GBSS gene and/or the SBE gene are to be disrupted via genome editing, a target sequence in the gene is selected, and a guide RNA sequence comprising a sequence complementary thereto may be designed. The nucleotide length of the guide RNA is preferably 20 or longer. When genome editing is performed by the CRISPR/Cas9 system, the Cas9 protein may be expressed in the presence of the guide RNA. For example, a vector expressing both thereof may be introduced. Genome editing performed by the CRISPR/Cas9 system can be performed with the use of a commercially available CRISPR/Cas9 equipment.

The vaccinia virus strain for producing the vaccinia virus of the present invention is not limited, and examples include strains such as Lister strain, LC16 strain, LC16mO strain, and LC16m8 strain established from the Lister strain (e.g., So Hashizume, Clinical Virology, Vol. 3, No. 3, 269, 1975,), New York City Board of Health (NYBH) strain, Wyeth strain, Copenhagen strain, Western Reserve (WR) strain, Modified Vaccinia Ankara (MVA) strain, EM63 strain, Ikeda strain, Dairen strain, and Tian Tan strain. The LC16mO strain is generated from the Lister strain via the LC16 strain. The LC16m8 strain is further generated from LC16mO strain, which is attenuated because a frameshift mutation had occurred in the B5R gene encoding a viral membrane protein and the protein became unexpressible and dysfunctional (PROTEIN, NUCLEIC ACID, AND ENZYME, Vol. 48, No. 12, 2003, pp. 1693-1700).

The vaccinia virus used in the present invention is preferably attenuated and is not pathogenic from the viewpoint of the established safety when it is administered to humans. An example thereof is a strain partially or completely deprived of the B5R gene. The B5R gene encodes the protein that is present in the vaccinia virus envelope and the B5R gene product is involved in viral infection and growth. The B5R gene product is present on the infected cell surface and in the virus envelope, it enhances the efficiency of infection when the virus infects and transmits to adjacent cells or other parts of the host body, and it is also involved in the plaque size and the host range of the virus. When animal cells are infected with the virus deprived of the B5R gene, the plaque size is reduced, and the pock size is also reduced. In addition, the ability of viruses to grow in the skin is lowered, and the pathogenicity in the skin is lowered. In the case of the vaccinia virus that is partially or completely deprived of the B5R gene, the B5R gene product does not have its normal functions, and the growth ability in the skin is low. Even if it is administered to a human, accordingly, no side effects would occur. An example of an attenuated strain deprived of the B5R gene is an m84 strain established from the LC16m8 strain by complete deprivation of the B5R gene (also referred to as "LC16m8Δ strain"). An mOΔ strain established from the LC16mO strain by complete deprivation of the B5R gene (also referred to as "LCmOΔ strain") can also be used. These attenuated vaccinia virus strains partially or completely deprived of the B5R gene are described in WO 2005/054451 and can be obtained in accordance with the description thereof. Whether or not the vaccinia virus is partially or completely deprived of the B5R gene and has lost the function of the B5R protein can be determined based on, for example, the size of the plaque and the size of the pock formed when RK13 cells are infection with the virus, the virus growth capacity in Vero cells, and the pathogenicity in the skin in rabbit as indicators. Alternatively, the gene sequence of the vaccinia virus may also be inspected.

The vaccinia virus having the B5R gene expresses the B5R gene in cancer cells and damages the cancer cells by the action of the B5R protein. Accordingly, it is preferable that the vaccinia virus used in the present invention express the complete B5R gene. When the attenuated vaccinia virus deprived of the B5R gene, and with established safety as described above is used, another complete B5R gene is further introduced into the vaccinia virus deprived of the B5R gene. When the vaccinia virus partially or completely deprived of the B5R gene is used, the B5R gene may be inserted into such a vaccinia virus genome and used in that state. The B5R gene may be inserted into the vaccinia virus by any method, such as a conventional method of homologous recombination. In such a case, the B5R gene may be inserted at a site between the B4R gene and the B6R gene where the B5R gene was originally present or at any site in the genome of the vaccinia virus. Alternatively, the B5R gene may be constructed as a DNA construct in advance and the DNA construct may be introduced into the vaccinia virus.

The vaccinia virus is deprived of the K2L gene or the HA gene and then loses functions of K2L or HA. This enhances the growth capacity and the transmissibility of the virus, oncolytic effects are potentiated, and cell death is then induced in the infected cancer cells. The term "cell death" used herein refers to both apoptosis and necrosis. Also, cell fusion is induced between the infected cancer cells. Upon induction of cell fusion, the ability of immunogenic cell death (ICD) induction is enhanced. As a result, CD8 T cells frequently infiltrate and attack cancer cells. In addition, a systemic anticancer immune activity is enhanced. Further, immunosuppressive cells, such as Treg, TAM, and MDSC, are decreased.

The vaccinia virus is deprived of the K2L gene or the HA gene and then loses functions of K2L or HA. As a result, the anticancer effects of the vaccinia virus are potentiated.

As a result of cell fusion occurred in the cells infected with the vaccinia virus, as described above, anticancer effects are potentiated, and the anticancer effects and the ability of ICD induction are improved regardless of tumor specificity. When the vaccinia virus has tumor specificity, anticancer effects are synergistically potentiated. Accordingly, the vaccinia virus used in the present invention is preferably an oncolytic virus that has tumor-cell-specific cytolytic effects and is capable of infecting cancer cells to induce cell death in the cancer cells. Such vaccinia virus is obtained by genetic modification, such as deletion of functions of a particular protein or suppression of expression of a particular gene or protein.

Examples of such genes include: hemagglutinin (HA) gene; thymidine kinase (TK) gene; F fragment; F3 gene; vaccinia virus growth factor (VGF) gene (U.S. Patent Application No. 2003/0031681); O1L; bleeding region or A-type inclusion body region (U.S. Pat. No. 6,596,279); HindIII F, F13L, or HindIII M region (U.S. Pat. No. 6,548,068); A33R, A34R, or A36R gene (Katz et al., J. Virology, 77: 12266-12275, 2003); SalF7L gene (Moore et al., EMBO J. 1992, 11: 1973-1980); N1L gene (Kotwal et al., Virology, 1989, 171: 579-58); M1 gene (Child et al., Virology. 1990 174: 625-629); HR, HindIII-MK, HindIII-MKF, HindIII-CNM, RR, or BamF region (Lee et al., J. Virol., 1992, 66: 2617-2630); and C21L gene (Isaacs et al., Proc. Natl. Acad. Sci., U.S.A., 1992, 89: 628-632). Of these genes, VGF gene, O1L gene, TK gene, HA gene, and F fragment are preferable.

A plurality of genetic modifications may be provided in combination. Examples of a plurality of genetic modifications include the following.

- Deletion of functions of TK, HA, and F14.5L (Cancer Research, 2007, Vol. 67, pp. 10038-10046) in combination with deletion of functions of TK and B18R (PLoS Medicine, 2007, Vol. 4, p. e353)
- Deletion of functions of TK and ribonucleotide reductase (PLoS Pathogens, 2010, Vol. 6, p. e1000984)
- Deletion of functions of SPI-1 and SPI-2 (Cancer Research, 2005, Vol. 65, pp. 9991-9998)
- Deletion of functions of SPI-1, SPI-2, and TK (Gene Therapy, 2007, Vol. 14, pp. 638-647)
- Introduction of mutation into E3L and K3L domains (WO 2005/007824)

The vaccinia viruses that are deprived of such gene functions and have oncolytic effects are referred to as "oncolytic vaccinia viruses."

A plurality of such genes may be deleted. For example, the VGF gene and the O1L gene may be deleted. The vaccinia virus deprived of functions of both of the VGF gene and the O1L gene is described in WO 2015/076422.

When the vaccinia virus is deprived of functions of the TK gene, for example, the growth capacity of the vaccinia virus is lowered in normal cells. In contrast, enzymes that supplement functions of the TK gene are abundant in cancer cells. Thus, the growth capacity of the vaccinia virus is not lowered in cancer cells. When the growth capacity is lowered in normal cells, pathogenicity against normal cells is lowered. When the virus is applied to living organisms, specifically, safety thereof is improved. When the vaccinia virus deprived of functions of the VGF gene and the O1L gene infects normal cells, ERK is not activated in normal cells, the cell growth is not promoted, and, as a consequence, the growth capacity of the vaccinia virus is lowered to a significant extent. In cancer cells, in contrast, the Ras/Raf/MEK/ERK metabolic pathway is activated to an abnormal extent, which supplements the ERK activation functions of VGF and O1L of the vaccinia virus, and the vaccinia virus can thus grow. As a result, the vaccinia virus grows in a cancer-cell-specific manner, and the virus disrupts and damages cancer cells.

With the use of the oncolytic vaccinia virus, the ability of cell fusion is enhanced as a result of deletion of the K2L gene or the HA gene, and the ability of cell death induction in cancer cells is synergistically enhanced.

The genes can be deleted by the techniques described above, such as genome editing, homologous recombination, RNA interference, the antisense method, gene insertion, artificial mutagenesis, or PTGS involving the use of a virus vector.

When the vaccinia virus is used for cancer virotherapy, the cancer to be targeted is not limited and examples thereof include a wide variety of cancer types, such as ovarian cancer, lung cancer, pancreatic cancer, skin cancer, stomach cancer, liver cancer, hepatic cell cancer, colorectal cancer, analrectal cancer, esophagus cancer, uterine cancer, breast cancer, bladder cancer, prostate cancer, testicular cancer, head and neck cancer, brainnerve tumors, thymic cancer, lymphoma, leukemia, bonecancer/osteo sarcoma, leiomyoma, rhabdomyoma, and melanoma.

The pharmaceutical composition for cancer therapy comprising the vaccinia virus of the present invention comprises, as an active ingredient, a pharmaceutically effective amount of the vaccinia virus of the present invention and may be in the form of a sterile aqueous or nonaqueous solution, suspension, or emulsion. Further, the composition may comprise a pharmaceutically acceptable diluent, aid, or carrier such as a salt, a buffer agent, and an adjuvant. Administration may be carried out via various parenteral routes, such as a subcutaneous, intravenous, intradermal, intramuscular, intraperitoneal, intranasal, or transdermal route. Additionally, local administration may be carried out to a cancer site. The effective dose can be adequately determined depending on, for example, the age, sex, health conditions, and body weight of a subject. While the dose is not limited, for example, it may be about $10^2$ to $10^{10}$ plaque-forming unit (PFU) per administration to a human adult.

The present invention also includes a method of cancer therapy comprising administering the vaccinia virus to a cancer patient.

The vaccinia virus of the present invention may further comprise a foreign gene (foreign DNA or foreign polynucleotide). Examples of the foreign gene (foreign DNA or foreign polynucleotide) include a marker gene, a therapeutic gene encoding a product having cytotoxic and immunostimulatory effects, and DNA encoding a protein antigen of a cancer, a virus, a bacterium, or a protozoan. The marker gene is also referred to as a reporter gene and examples include fluorescent protein genes such as luciferase (LUC) gene and green fluorescent protein (GFP), fluorescent protein genes such as red fluorescent protein (DsRed), β glucuronidase (GUS) gene, chloramphenicol acetyltransferase (CAT) gene, and β-galactosidase (LacZ) gene. An oncolytic vaccinia virus comprising such foreign gene can also be referred to as a vaccinia virus vector.

Therapeutic genes can be used for treatment of particular diseases, such as cancers and infectious diseases, and examples thereof include: tumor suppressor genes, such as p53 and Rb; genes encoding physiologically active substances, such as interleukin 1 (IL-1), IL-2, IL-3, IL-4, IL-5, IL-6, IL-7, IL-8, IL-9, IL-10, IL-11, IL-12, IL-13, IL-14, IL-15, IL-17, IL-18, IL-24, chemokine 2 (CCL2), CCL5, CCL19, CCL21, CXCL9, CXCL10, CXCL11, CD40L, CD70, CD80, CD137L, OX-40L, GITRL, LIGHT, α-interferon, β-interferon, γ-interferon, angiostatin, thrombospondin, endostatin, METH-1, METH-2, GM-CSF, G-CSF, M-CSF, MIP1a, FLT3L, HPGD, TRIF, DAI, and a tumor necrosis factor; and genes encoding antibodies having inhibitory activity on CTLA4, PD1, and PD-L1. A luciferase- or GFP-expressing vaccinia virus is capable of infecting cancer cells and detecting the cancer cells infected therewith easily and rapidly. When the vaccinia virus of the present invention is used for cancer therapy, the vaccinia virus can exert oncolytic effects and a therapeutic gene for cancer can exert therapeutic effects on cancer.

When DNA encoding an antigen of a virus, a bacterium, a protozoan, or a cancer is introduced as a foreign gene (foreign DNA), the vaccinia virus comprising the foreign gene introduced thereinto can be used as the vaccine against various viruses, bacteria, protozoans, and cancers. For example, genes encoding infection protective antigens (neutralizing antigens) of human immunodeficiency virus, hepatitis virus, herpes virus, micobacterium, malaria plasmodium, or severe acute respiratory syndrome (SARS) virus, genes encoding cancer antigens of proteins, such as WT1, MART-1, NY-ESO-1, MAGE-A1, MAGE-A3, MAGE-A4, Glypican-3, KIF20A, Survivin, AFP-1, gp100, MUC1, PAP-10, PAP-5, TRP2-1, SART-1, VEGFR1, VEGFR2, NEIL3, MPHOSPH1, DEPDC1, FOXM1, CDH3, TTK, TOMM34, URLC10, KOC1, UBE2T, TOPK, ECT2, MESOTHELIN, NKG2D, P1A, 5T4, B7-H6, BCMA, CD123, CD133, CD138, CD171, CD19, CD20, CD22, CD23, CD30, CD33, CD38, CD44, CEA, cMet, CS1, EGFR, EGFRvIII, EphA2, ErbB2, FAP, FR-α, HER2, IL13Ra2, MUC1, MUC16, NKG2D, PSCA, PSMA, ROR1, TARP, DLL3, PRSS21, Claudin18.2, Claudin18, CAIX, L1-CAM, FAP-α, CTAG1B, and FR-α, or genes encoding cancer antigens of glycolipids, such as GD2 and GM2, may be introduced.

These foreign genes can be introduced by, for example, homologous recombination. Homologous recombination may be carried out in the manner described above. For example, a plasmid in which a foreign gene to be introduced is ligated to a DNA sequence of a site of interest (i.e., a transfer vector) may be prepared, and the transfer vector may be introduced into a cell infected with the vaccinia virus. It is preferable that the foreign gene be introduced into a gene that is not essential for the life cycle of the vaccinia virus.

When the foreign gene is introduced, it is preferable that an adequate promoter be operably linked to a site upstream of the foreign gene. The promoter is not limited, and PSFJ1-10, PSFJ2-16, p7.5K promoter, p11K promoter, T7.10 promoter, CPX promoter, HF promoter, H6 promoter, T7 hybrid promoter, or the like as described above can be used. The method for introducing the foreign gene into the vaccinia virus vector of the present invention can be carried out by a known method for constructing a recombinant vaccinia virus vector in accordance with, for example, Experimental Medicine Supplement, the protocol series, Gene transfer & Experimental method of analyzing expression, edited by Izumi Saito et al. (date of publication: Sep. 1, 1997, YODOSHA CO., LTD.) or DNA Cloning 4-Mammalian Systems-(2nd edition) TaKaRa, EMBO Journal, 1987, vol. 6, pp. 3379-3384, edited by D. M. Glover et al.; supervised by Ikunoshin Kato.

The present invention includes therapy involving the use of the vaccinia virus having the ability of cell fusion in combination with the immune checkpoint inhibitor.

Examples of immune checkpoint inhibitors include anti-PD-1 (programmed cell death 1) antibody, anti-PD-L1 (programmed cell-death ligand 1) antibody, anti-CTLA-4 antibody, anti-PD-L2 antibody, anti-LAG-3 antibody, PD-1 antagonist, and PD-L1 antagonist. Among them, the anti-PD-1 antibody and the anti-PD-L1 antibody are preferable. Examples of the anti-PD-1 antibody include Nivolumab, Pembrolizumab, Spartalizumab, Cemiplimab, Tislelizumab, and Camrelizumab. Examples of the anti-PD-L1 antibody include Avelumab, Durvalumab, and Atezolizumab.

The immune checkpoint inhibitor may be administered in accordance with a conventional technique. While the amount of the immune checkpoint inhibitor to be administered varies depending on the symptom, the age, the body weight, and other conditions, for example, 0.001 mg to 100 mg of the immune checkpoint inhibitor may be administered at intervals of several days, several weeks, or several months by means of hypodermic, intramuscular, or intravenous injection.

The immune checkpoint inhibitor may be supplemented with, for example, a carrier, a diluent, and an excipient generally used in the field of pharmaceutical preparation. Examples of carriers and excipients that can be used for tablets include lactose and magnesium stearate. An example of an aqueous solution for injection is an isotonizing liquid containing physiological saline, glucose, and other adjuvants. An alcohol, a polyalcohol such as propylene glycol, and a solubilizer such as a nonionic surfactant may be used in combination. As an oil, sesame oil, soybean oil, or the like may be used, and a solubilizer, such as benzyl alcohol or benzyl alcohol, may be used in combination.

The vaccinia virus having the ability of cell fusion and the immune checkpoint inhibitor of the present invention can exert synergistic effects in cancer therapy. When the vaccinia virus having the ability of cell fusion is used in combination with the immune checkpoint inhibitor, cancer therapeutic effects would be significantly higher than the cancer therapeutic effects achieved when the vaccinia virus having the ability of cell fusion or the immune checkpoint inhibitor is used by itself.

The vaccinia virus having the ability of cell fusion and the immune checkpoint inhibitor of the present invention can be administered simultaneously, separately, or continuously.

The vaccinia virus having the ability of cell fusion can be administered before or after the immune checkpoint inhibitor is administered. It is preferable that the vaccinia virus having the ability of cell fusion be administered before the immune checkpoint inhibitor is administered.

The present invention also encompasses a combination, a combination formulation, or a combination pharmaceutical kit comprising the vaccinia virus having the ability of cell fusion and the immune checkpoint inhibitor.

The present invention also encompasses a method for producing a pharmaceutical product used for cancer therapy involving the use of the vaccinia virus having the ability of cell fusion in combination with the immune checkpoint inhibitor.

The present invention also encompasses a pharmaceutical product comprising the vaccinia virus having the ability of cell fusion and the immune checkpoint inhibitor.

The present invention further encompasses the vaccinia virus having the ability of cell fusion to be used in combination with the immune checkpoint inhibitor.

EXAMPLES

The present invention is described in detail with reference to the following examples, although the present invention is not limited to these examples.

Example 1

Structure of the Vaccinia Virus Having the Ability of Cell Fusion

In order to insert different foreign gene expression units into the VGF gene and the O1L gene of the mitogen-activated protein kinase-dependent recombinant vaccinia virus that is deprived of functions of VGF and O1L (WO 2015/076422), the BFP gene region was amplified by PCR using, as a template, DNA of pTagBFP-N (FP172, Evrogen) and two primers (SEQ ID NO: 1 and SEQ ID NO: 2). The PCR products were cleaved with the restriction enzymes SfiI and EcoRI, and the cleavage products were cloned into the same restriction enzyme site of the pTK-SP-LG vector (WO 2015/076422) to construct pTNshuttle/TK-SP-BFP comprising the synthetic vaccinia virus promoter (Hammond J. M. et al., Journal of Virological Methods, 1997; 66 (1): 135-138) and BFP ligated to a site downstream thereof. Subsequently, pTNshuttle/TK-SP-BFP was cleaved with the restriction enzymes SphI and EcoRI, the cleavage product was blunt-ended, the SP-BFP fragment was cloned into a site resulting from cleavage of the pUC19-VGF vector (WO 2015/076422) with the restriction enzyme AccI and blunt ending or a site resulting from cleavage of the pUC19-O1L vector (WO 2015/076422) with the restriction enzyme XbaI and blunt ending, and a shuttle vector pTNshuttle/VGF-ST-BFP to express BFP in the opposite direction from VGF or pTNshuttle/O1L-SP-BFP to express BFP in the opposite direction from O1L was constructed. In the same manner as in WO 2015/076422, pUC19-O1L-P-DsRed to express DsRed in the same direction with O1L downstream of the p7.5K promoter instead of the synthetic vaccinia virus promoter was constructed. The CV1 cells that had been cultured to 80% confluence in a 24-well plate were infected with VGF-LucGFP/O1L-DsRed at MOI of 0.1 to 0.5, and the viruses were allowed to adsorb to the cells at room temperature for 1 hour. Thereafter, FuGENE HD (Roche) was mixed with the transfer vector plasmid (pTNshuttle/O1L-SP-BFP) in accordance with the instructions, the resultant was incorporated into the cells, and culture was conducted at 37° C. for 2 to 3 days. The cells were collected, freeze-thawed, sonicated, adequately diluted, and inoculated into the BSC1 cells that had almost reached confluence. Eagle MEM containing 0.5% methyl cellulose and 5% FBS medium were added, and culture was conducted at 37° C. for 2 to 4 days. The media were removed, BFP-expressing plaques were scraped with a chip end, and the plaques were suspended in Opti-MEM medium (Invitrogen). This procedure was repeated 3 or more times with the BSC1 cells to purify the plaques. The plaque suspension sampled after plaque purification was sonicated, genomic DNA was extracted from 200 µl of the suspension with the use of the High Pure Viral Nucleic Acid Kit (Roche) in accordance with the instructions, and the extracted genomic DNA was subjected to screening via PCR. O1L was subjected to PCR with the use of two primers (SEQ ID NO: 3 and SEQ ID NO: 4), and clones in which PCR products of given sizes had been detected were examined in terms of their nucleotide sequences via direct sequencing. Virus clones not presenting any problems in terms of nucleotide sequences (VGF-LucGFP/O1L-BFP) were selected, amplified in A549 cells, subjected to virus titer measurement in the RK13 cells, and then subjected to experimentation. On the basis of the vaccinia virus (VGF-LucGFP/O1L-BFP) and plasmid DNA of the transfer vector (pUC19-O1L-P-DsRed), recombinant viruses were collected in the same manner as described above using DsRed expression as the indicator and designated as VGF-LucGFP/O1L-DsRed.

During the process of preparing the gene recombinant vaccinia viruses, viruses having the unusual ability of cell fusion appeared at very high frequency. Thus, the media were removed, and plaques having character of fusion were scraped with a chip end, and the plaques were suspended in Opti-MEM medium (Invitrogen). This procedure was repeated 3 or more times with the BSC1 cells, and 2 virus clones having the ability of cell fusion were obtained by plaque purification. These 2 clones were subjected to direct sequencing by means of the next-generation sequencer (PacBio RSII, Pacific Bioscience) or PCR. The resulting sequence information demonstrates that a mutation is detected in the K2L or HA gene and that the clones comprise the nucleotide sequence as shown in SEQ ID NO: 5 or SEQ ID NO: 6. K2L is a gene with a full length of 1,110 bp in which guanine at position 762 had been mutated into adenine. This indicates that amino acid tryptophan-254 is changed to a stop codon; that is, a nonsense mutation has occurred. HA is a gene with a full length of 933 bp deprived of adenine at position 70. This indicates that a frameshift mutation has occurred. The 2 virus clones having the ability of cell fusion were designated as VGF-LucGFP/K2Lmut/O1L-DsRed and VGF-LucGFP/O1L-BFP/HAmut (FIG. 1B and FIG. 1C), respectively, based on the parent virus VGF-LucGFP/O1L-DsRed (WO 2015/076422) (FIG. 1A). The recombinant viruses were mass-cultured in A549 cells, purified, subjected to virus titer measurement in RK13 cells, and then subjected to experimentation.

Subsequently, the Luc2 gene region was amplified by PCR using, as a template, DNA of pGL4.20 (F6751, Promega Corporation) and 2 primers (SEQ ID NO: 7 and SEQ ID NO: 8). The PCR products were cleaved with the restriction enzymes BspEI and NheI, the cleavage products were cloned into the restriction enzyme sites AgeI and NheI of the pTNshuttle/VGF-SP-BFP vector to be substituted with the BFP gene, and pTNshuttle/VGF-SP-Luc was thus constructed. The *E. coli* LacZ gene synthesized to be codon-optimized with *H. sapiens* (SEQ ID NO: 9) was cleaved with the restriction enzymes AgeI and NheI, the cleavage products were cloned into the same restriction enzyme sites of the pTNshuttle/O1L-SP-BFP vector to be substituted with the BFP gene, and pTNshuttle/O1L-SP-LacZ was thus constructed.

In order to collect the recombinant vaccinia viruses having the virus genome as shown in FIG. 1B, based on the vaccinia viruses (VGF-LucGFP/O1L-DsRed or VGF-LucGF P/K2Lmut/O1L-DsRed) and plasmid DNA of the transfer vector (pTNshuttle/VGF-SP-Luc), recombinant viruses were collected in the same manner as described above with the use of GFP quenching as the indicator and designated as VGF-Luc/O1L-DsRed or VGF-Luc/K2Lmut/O1L-DsRed. Based on the vaccinia viruses (VGF-Luc/O1L-DsRed or VGF-Luc/K2Lmut/O1L-DsRed) and plasmid DNA of the transfer vector (pTNshuttle/O1L-SP-LacZ), recombinant viruses were collected in the same manner as described above with the use of DsRed quenching as the indicator and subjected to screening by PCR. VGF was subjected to PCR using 2 primers (SEQ ID NO: 10 and SEQ ID NO: 11), K2L was subjected to PCR using 2 primers (SEQ ID NO: 12 and SEQ ID NO: 13), and clones in which PCR products of given sizes had been detected were examined in terms of their nucleotide sequences via direct sequencing. Virus clones not presenting any problems in terms of nucleotide sequences were designated as VGF-Luc/O1L-LacZ or VGF-Luc/K2Lmut/O1L-LacZ (FIG. 1D and FIG. 1E). The recombinant viruses were mass-cultured in A549 cells, purified, subjected to virus titer measurement in RK13 cells, and then subjected to experimentation.

Example 2

Analysis of Properties of the Vaccinia Virus Having the Ability of Cell Fusion

Figure 2:
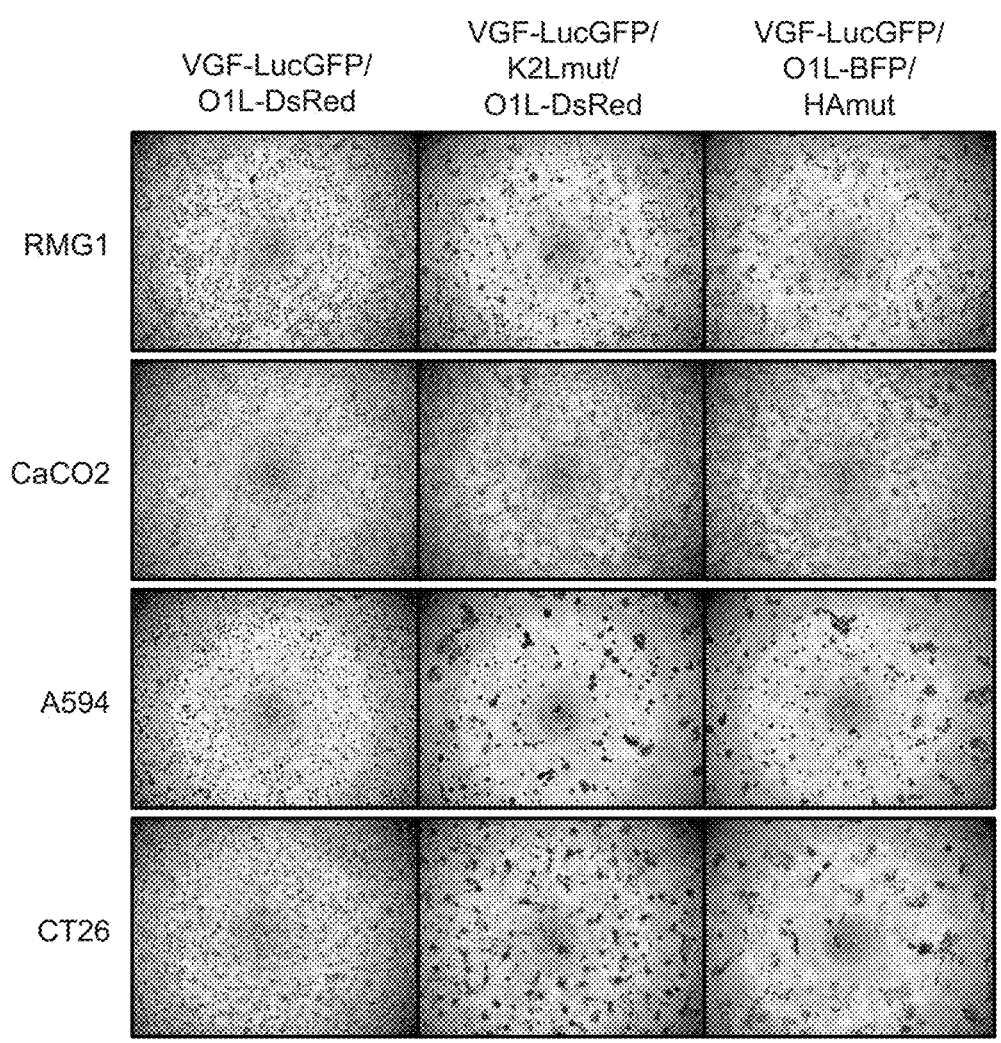
FIG. 2 shows images of cells infected with the cell fusion-inducing gene recombinant vaccinia viruses.

In order to compare VGF-LucGFP/O1L-DsRed not having the ability of cell fusion with VGF-LucGFP/K2Lmut/O1L-DsRed and VGF-LucGFP/O1L-BFP/HAmut having the ability of cell fusion, cells were infected with the viruses. At the outset, various cancer cells (i.e., human ovarian cancer RMG1 cells, human colon cancer CaCO2 cells, human lung cancer A549 cells, and mouse colon cancer CT26 cells) were sowed on 96-well plates (RMG1 and CaCO2: $2.0\times10^4$ cells/well; A549: $1.0\times10^4$ cells/well; CT26: $6.0\times10^3$ cells/well), the cells were cultured to 80% confluence for 24 hours, and RMG1, CaCO2, and A549 were infected with VGF-LucGFP/O1L-DsRed, VGF-LucGFP/K2Lmut/O1L-DsRed, or VGF-LucGFP/O1L-BFP/HAmut at MOI of 0.1 and CT26 was infected therewith at MOI of 10. Images of the infected cells were observed using BZ-X700 (Keyence) 72 hours after infection. As a result, VGF-LucGFP/K2Lmut/O1L-DsRed and VGF-LucGFP/O1L-BFP/HAmut were found to infect various cancer cells while allowing the infected cells to fuse to each other, compared with VGF-LucGFP/O1L-DsRed (FIG. 2).

Figures 1, 3:
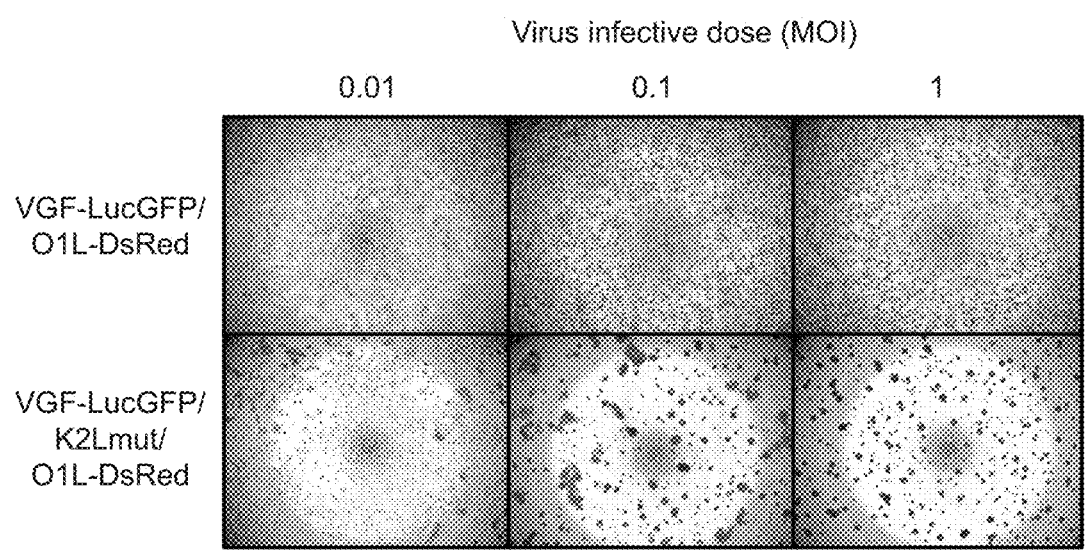
Figures 2, 3:
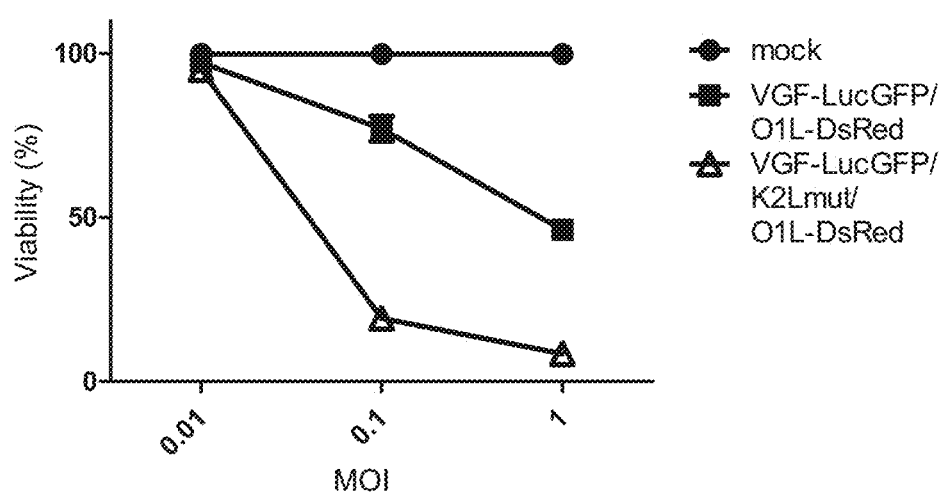
Figure 3:
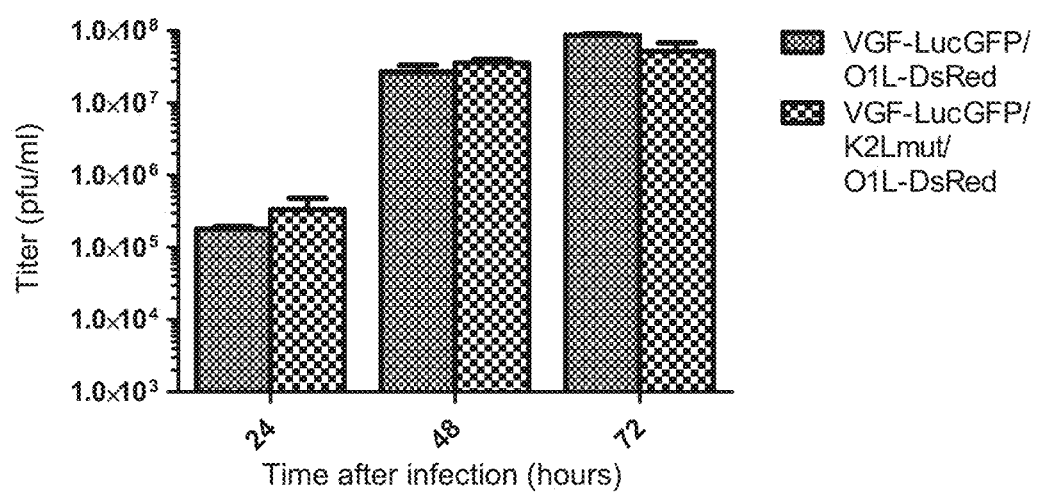

Whether or not cell fusion would affect anticancer effects was then inspected with the use of VGF-LucGFP/O1L-DsRed and VGF-LucGFP/K2Lmut/O1L-DsRed. At the outset, A549 cells were sowed on a 96-well plate at $1.0\times10^4$ cells/well, the cells were cultured to 80% to 90% confluence for 24 hours, and the culture products were then infected with virus solutions at MOI of 0.01, 0.1, and 1. Images of the infected cells were observed using BZ-X700 (Keyence) 72 hours after infection. As a result, VGF-LucGFP/K2Lmut/O1L-DsRed was found to infect various cancer cells while allowing the infected cells to fuse to each other in an MOI-dependent manner, compared with VGF-LucGFP/O1L-DsRed. FIG. 3-1 shows images of infected cells. Cell viability was assayed using CellTiter96® Aqueous Nonradioactive Cell Proliferation Assay (Promega) 72 hours after infection. As a result, VGF-LucGFP/K2Lmut/O1L-DsRed was found to exhibit lower cell viability at MOI of 0.1 and 1 and improved anticancer effects, compared with VGF-LucGFP/O1L-DsRed. FIG. 3-2 shows cytotoxicity in terms of cell viability. In order to inspect as to whether or not the amount of virus production would vary as a result of cell fusion, the amount of viruses produced by VGF-LucGFP/O1L-DsRed was compared with that by VGF-LucGFP/K2Lmut/O1L-DsRed by measuring the virus titers (titration). At the outset, human lung cancer A549 cells were sowed as host cells on a 24-well plate at $5.0\times10^4$ cells/well, cultured to 60% to 80% confluence for 24 hours, and then infected with virus solutions at MOI of 0.1. The cells and the supernatant were collected using a scraper 24, 48, and 72 hours after infection, the cells were disrupted by freeze-thawing and sonication, the resultants were centrifuged at 2,000 rpm and 4° C. for 10 minutes, and the supernatant was then collected. The virus titers were measured by sowing RK13 cells and changing dilution factors in accordance with the putative virus titers. The RK13 cells sowed on a 12-well plate at 80% confluence were infected with serially-diluted viruses ($10^{-1}$- to $10^{-5}$-fold diluted), culture was conducted in Eagle MEM containing 0.8% methyl cellulose and 5% FBS medium for 3 days, and the number of formed virus plaques was counted to determine the virus titers. As a result, no differences were observed between the amount of viruses produced by VGF-LucGFP/O1L-DsRed and that by VGF-LucGFP/K2Lmut/O1L-DsRed. FIG. 3-3 shows the amount of virus production in terms of the virus titer.

Example 3

Anticancer Effects of the Vaccinia Virus Having the Ability of Cell Fusion

Subsequently, viability of cells other than A549 was inspected using a wide variety of human and mouse cancer cells. Human ovarian cancer cells (SKOV3: $2.0\times10^4$ cells/well), human pancreatic cancer cells (Panc1: $2.0\times10^4$ cells/well), human colon cancer cells (CaCO2: $2.0\times10^4$ cells/well), human breast cancer cells (MDA-MB-231: $2.0\times10^4$ cells/well), human lung cancer cells (A549: $1.0\times10^4$ cells/well), human prostate cancer cells (PC3: $2.5\times10^4$ cells/well), human skin cancer cells (A431: $2.0\times10^4$ cells/well), mouse melanoma cells (B16-F10: $1.5\times10^4$ cells/well), mouse colon cancer cells (CT26: $1.0\times10^4$ cells/well), and mouse lung cancer cells (TC1: $4.0\times10^3$ cells/well) were sowed on 96-well plates, cultured at 37° C. for 24 hours, and then infected with virus solutions of VGF-LucGFP/O1L-DsRed or VGF-LucGFP/K2Lmut/O1L-DsRed. Panc1, CaCO2, MDA-MB-231, A549, and A431 were infected at MOI of 0.1, SKOV3 and PC3 were infected at MOI of 1, and B16-F10, CT26, and TC1 were infected at MOI of 5 (n=3). TC1 was subjected to cell viability measurement by means of CellTiter 96® Aqueous Nonradioactive Cell Proliferation Assay (Promega) 48 hours after infection, and other cells were subjected to cell viability measurement 72 hours after infection.

Figures 2, 4:
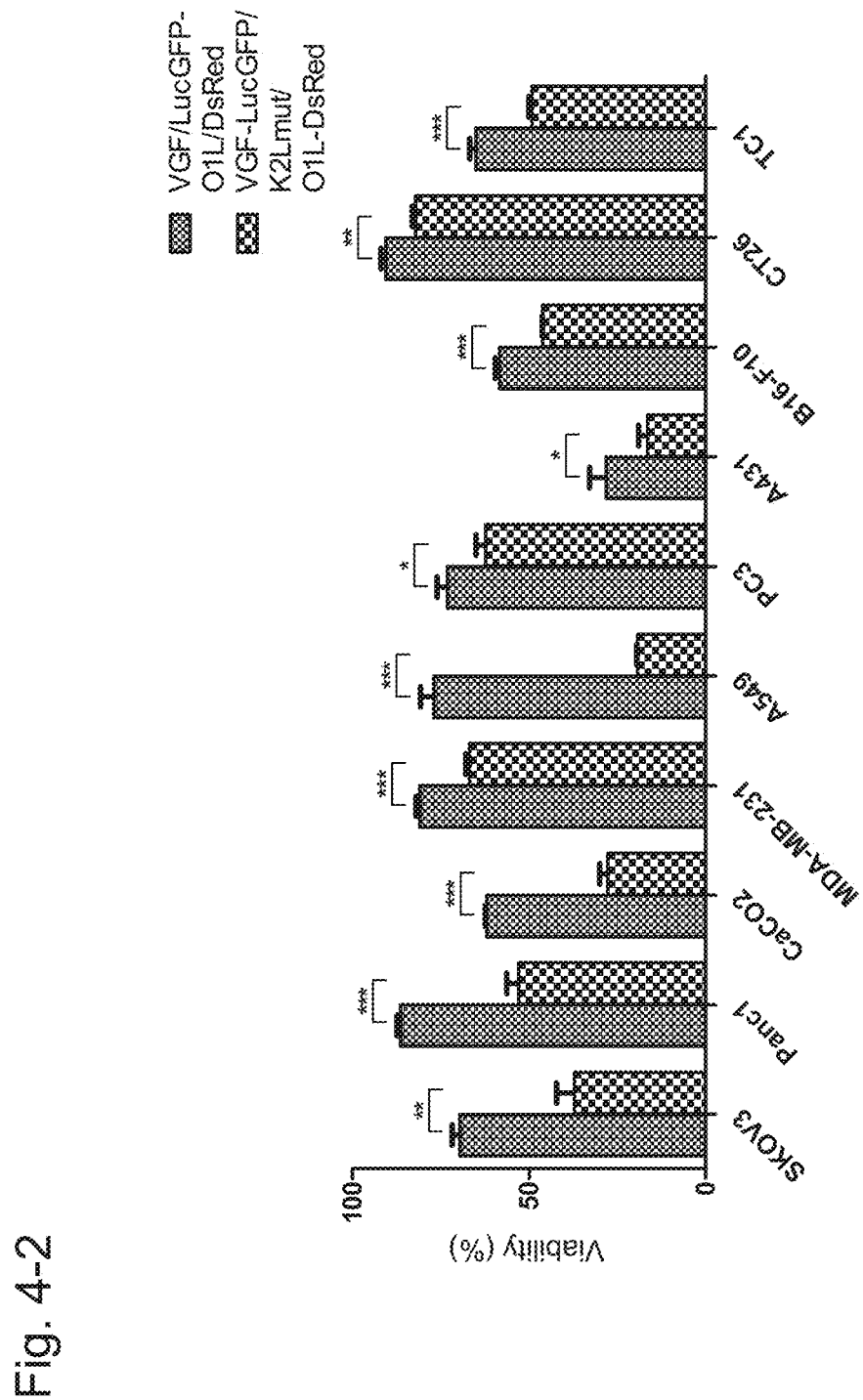

The images of infected cells demonstrate that cell fusion had occurred when infected with VGF-LucGFP/K2Lmut/O1L-DsRed. Specifically, the images of a wide variety of cancer cells infected with VGF-LucGFP/K2Lmut/O1L-DsRed were different from those infected with VGF- LucGFP/O1L-DsRed (FIG. 4-1). As a result of the t-test, in addition, VGF-LucGFP/K2Lmut/O1L-DsRed was found to lower the cell viability to a significant extent, compared with VGF-LucGFP/O1L-DsRed (SKOV3: P=0.0021, Panc1: *P=0.0003, CaCO2: *P<0.0001, MDA-MB-231: *P=0.0004, A549: ***P<0.0001, PC3: *P=0.0284, A431: *P=0.0480, B16-F10: *P=0.0004, CT26: P=0.0030, TC1: ***P=0.0006). Thus, VGF-LucGFP/K2Lmut/O1L-DsRed was found to exhibit improved antitumor effects on a wide variety of cancer types (FIG. 4-2).

Example 4

Analysis of Mechanisms of Anticancer Effects of the Vaccinia Virus Having the Ability of Cell Fusion In Vitro With the use of the Apoptotic/Necrotic/Healthy Cells Detection Kit (Takara Bio), whether or not apoptosis and necrosis had occurred at significant levels in human lung cancer cells (A549) and mouse colon cancer cells (CT26) was inspected. At the outset, A549 or CT26 cells were sowed on a 96-well plate at $1.0 \times 10^4$ cells/well, cultured at 37° C. for 24 hours, and then infected with virus solutions of VGF-Luc/O1L-LacZ or VGF-Luc/K2Lmut/O1L-LacZ. A549 was infected at MOI of 1 and CT26 was infected at MOI of 10 (n=3). The infected cells were assayed using the kit described above 30 or 22 hours after infection, the images thereof were obtained using BZ-X700 (Keyence), and the results were then quantified. As a result of the t-test, the number of cells detected as those that had undergone apoptosis caused by VGF-Luc/K2Lmut/O1L-LacZ was found to be significantly higher than that caused by VGF-Luc/O1L-LacZ in both A549 and CT26 (A549: *P=0.0355; CT26: *P=0.0264). As a result of the t-test, in addition, the number of cells detected as those that had undergone necrosis as well as apoptosis caused by VGF-Luc/K2Lmut/O1L-LacZ was found to be significantly higher (FIG. 5; A549: *P=0.0181; CT26: *P=0.0264). Also, immunogenic cell death (ICD), which is critical for induction of anti-tumor immunity, was examined As a mechanism of induction of immunity by ICD, for example, extracellular release of HMGB1 and cell surface exposure of Calreticulin have been reported. Extracellular HMGB1 was quantified using the HMGB1 ELISA Kit II (Shino-Test Corporation) herein. A549 cells and CT26 cells were sowed on a 24-well plate at $5.25 \times 10^4$ cells/well and $3.15 \times 10^4$ cells/well, cultured at 37° C. for 24 hours, and then infected with virus solutions of VGF-Luc/O1L-LacZ or VGF-Luc/K2Lmut/O1L-LacZ at MOI of 1 and MOI of 5 (n=3). The culture supernatant was collected 60 hours after infection and subjected to ELISA. As a result of the t-test, the extracellular release level of HMGB1 was increased by VGF-Luc/K2Lmut/O1L-LacZ to a significant extent, compared with VGF-Luc/O1L-LacZ, in both A549 and CT26 (FIG. 6) (A549: *P=0.0006; CT26: *P=0.0004). The results demonstrate that VGF-Luc/K2Lmut/O1L-LacZ would improve the ability of apoptosis and necrosis induction and that the enhanced ability for inducing anti-tumor immunity by ICD would potentiate anticancer effects.

Example 5

Therapeutic Effects of the Vaccinia Virus Having the Ability of Cell Fusion In Vivo Subsequently, viral growth and transmission in vivo and the therapeutic effects of viruses were examined using allogeneic transplantation mouse models.

Figure 7:
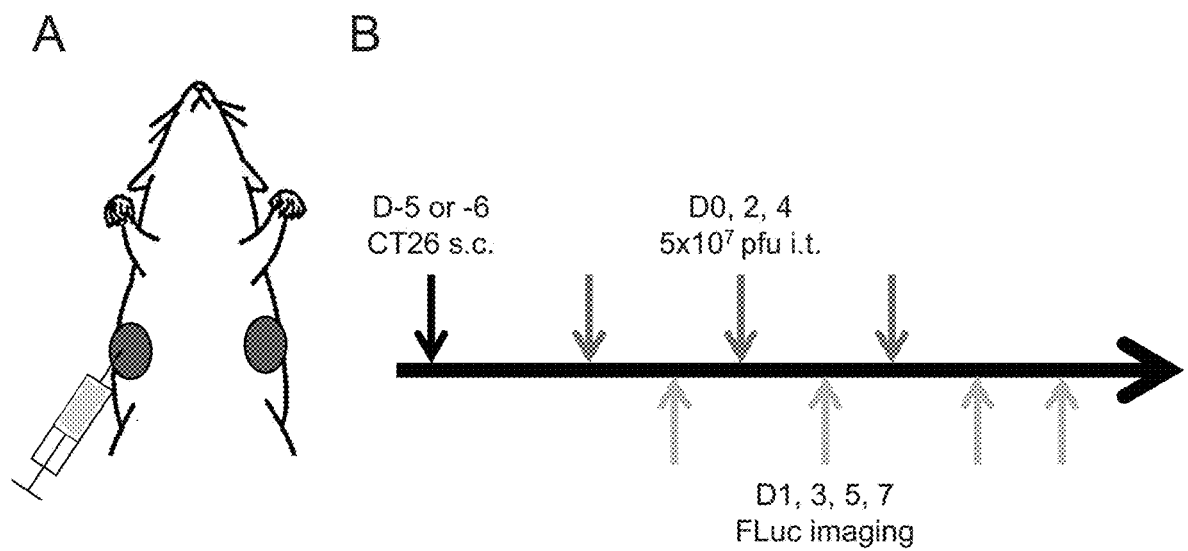
FIG. 7 shows an experimental system using allogeneic transplantation mouse models.
Figures 1, 8:
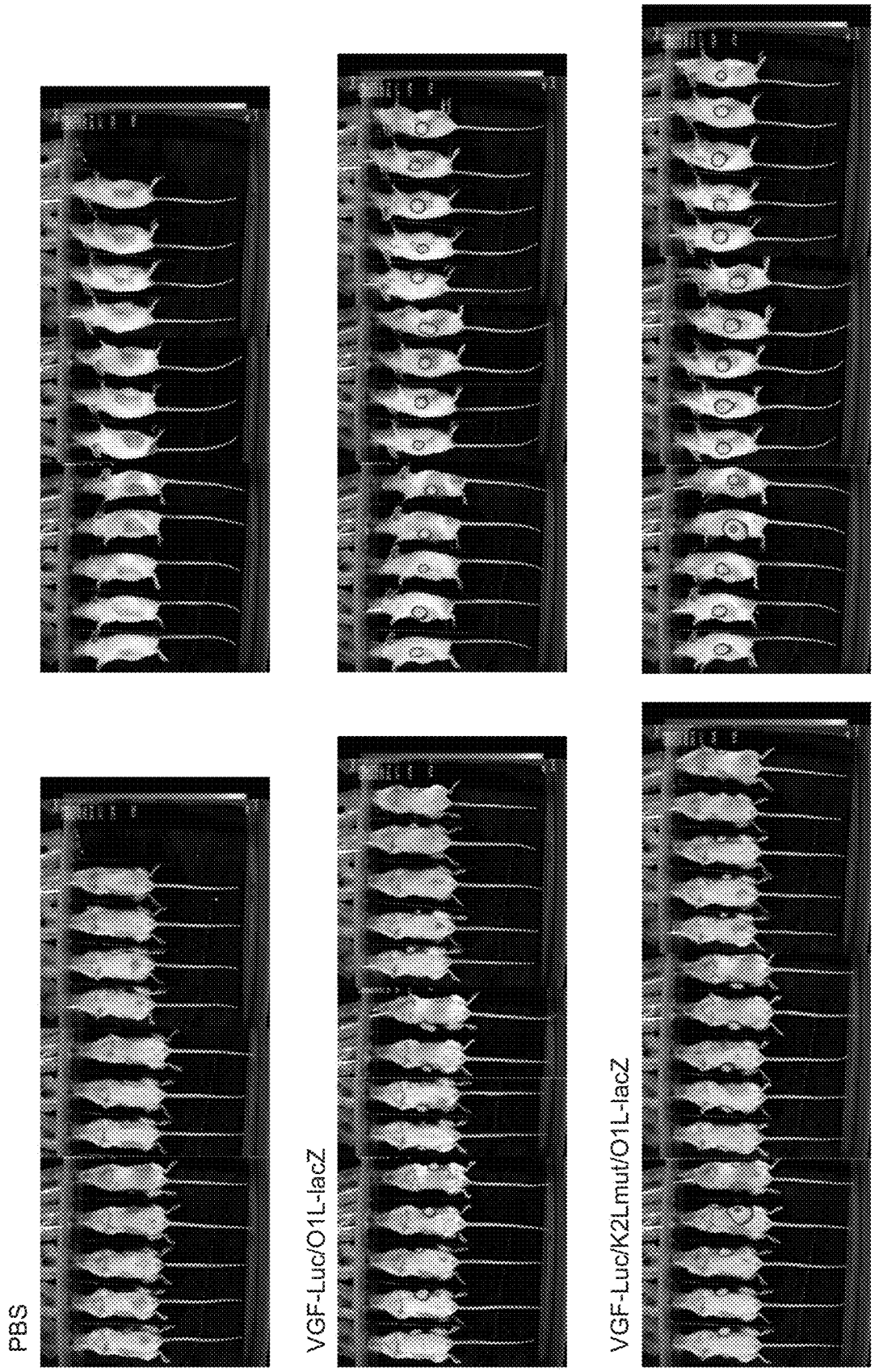
Figures 2, 8:
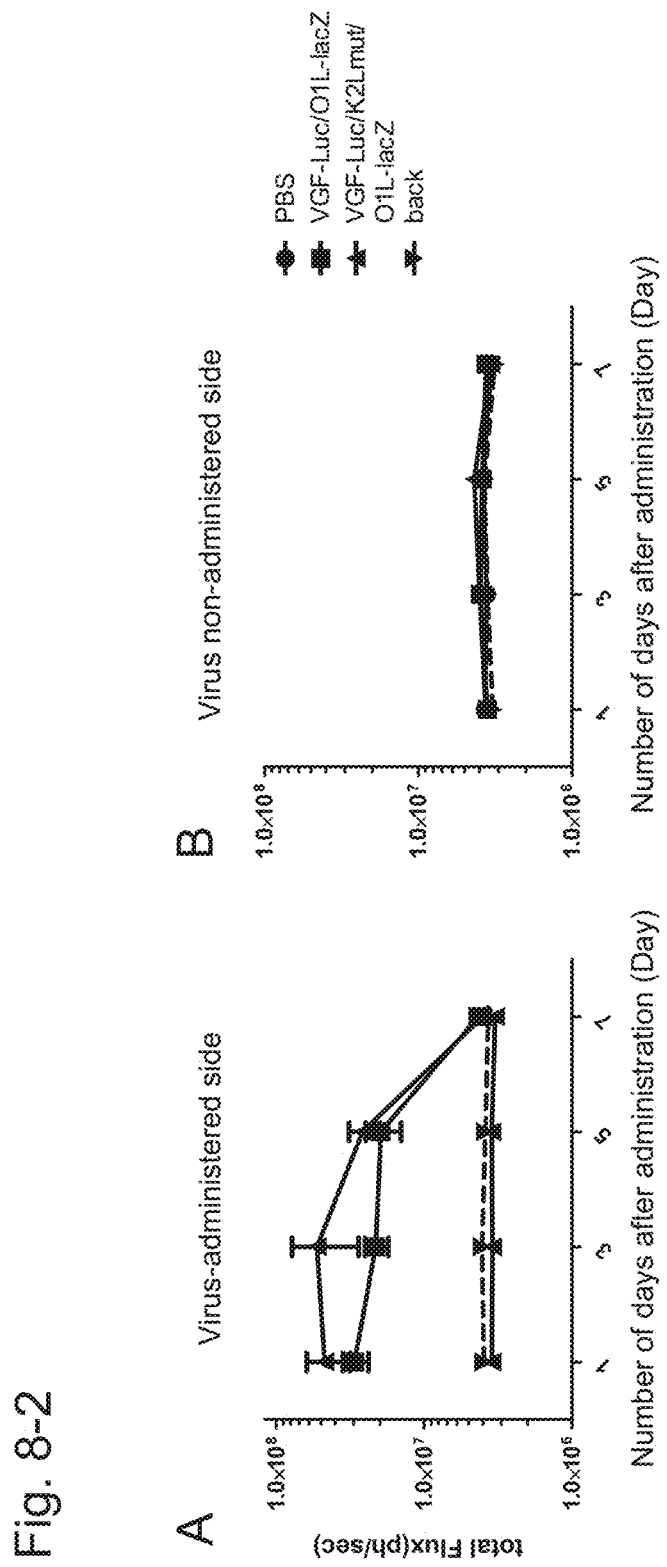
Figure 9:
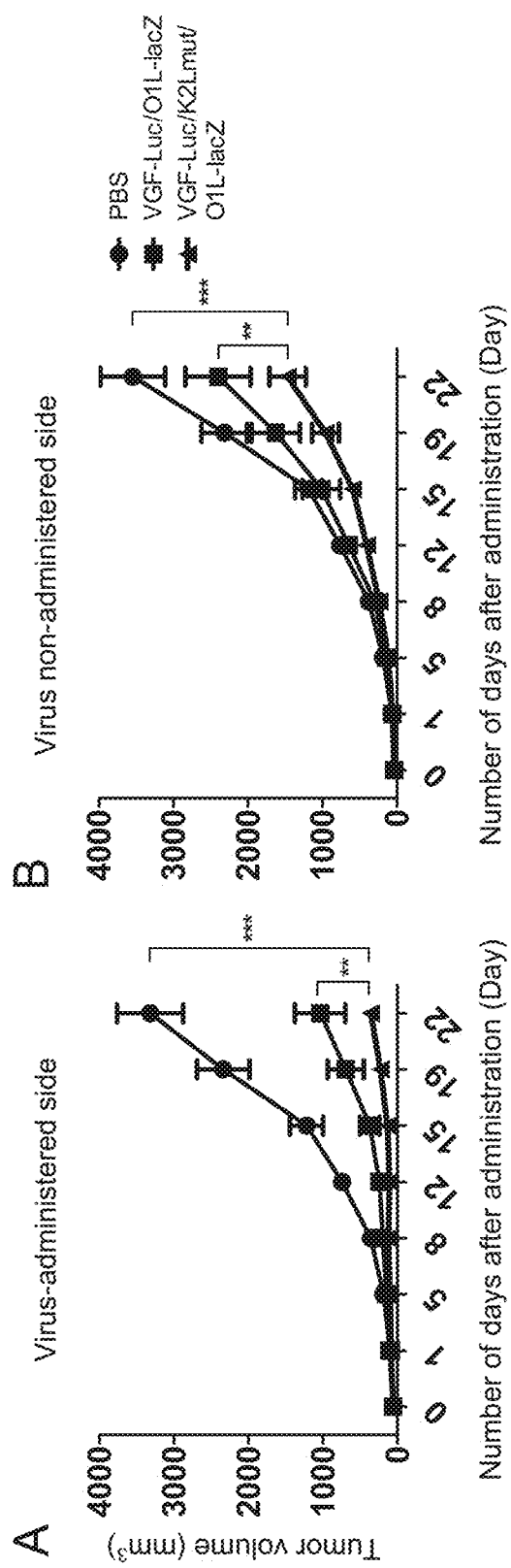
FIG. 9 shows the tumor volume in the allogeneic transplantation mouse models after the therapy with the cell fusion-inducing gene recombinant vaccinia viruses.

Mouse colon cancer cells (CT26) were transplanted subcutaneously to both sides of the abdominal region of the BALB/cAjcl mice at $5.0 \times 10^5$ cells, and the tumors were allowed to grow to the volumes of 42 to 94 mm$^3$ (average: 60 mm$^3$) for 5 or 6 days (FIG. 7A). After the tumors had grown, VGF-Luc/O1L-LacZ and VGF-Luc/K2Lmut/O1L-LacZ were administered directly to the tumor on one side at $5.0 \times 10^7$ PFU every other day (3 instances in total) (Days 0, 2, and 4). Also, FLuc luminescence of viruses (nearly equal to viral growth and transmission) was detected in a non-invasive manner by administering Vivo Glo Luciferin (Promega) and using the in vivo imaging system (Berthold, NightSHADE LB985) (Days 1, 3, 5, and 7) (FIG. 7B). FIG. 8-1 shows the results of detection of FLuc luminescence of viruses 3 days after virus administration. Concerning FLuc luminescence, VGF-Luc/K2Lmut/O1L-LacZ was observed to express signals at higher intensity on the virus-administered side, compared with VGF-Luc/O1L-LacZ, 3 days after virus administration. On the virus non-administered side, in contrast, no signaling was detected even if the viruses had been administered. When the FLuc expression levels were quantified, in addition, a significant difference was observed on the virus-administered side as a result of Two-Way ANOVA statistic analysis 3 days after virus administration (*P<0.05) (FIG. 8-2). The results demonstrate that viruses would more actively grow and transmit in vivo with the aid of VGF-Luc/K2Lmut/O1L-LacZ, compared with VGF-Luc/O1L-LacZ. Subsequently, therapeutic effects of viruses were examined by measuring tumor diameters. As a result, the tumor growth in the mice to which VGF-Luc/K2Lmut/O1L-LacZ had been administered was found to have been more effectively suppressed both on the virus-administered side and on the virus non-administered side, compared with the mice to which no viruses had been administered (PBS mice) and the mice to which VGF-Luc/O1L-LacZ had been administered. In addition, the mice to which VGF-Luc/K2Lmut/O1L-LacZ had been administered were found to exhibit significant differences in tumor volumes both on the virus-administered side and on the virus non-administered side, compared with PBS mice and the mice to which VGF-Luc/O1L-LacZ had been administered 22 days later, as a result of Two-Way ANOVA statistic analysis (P<0.01, *P<0.001) (FIG. 9).

Example 6

Figures 1, 10:
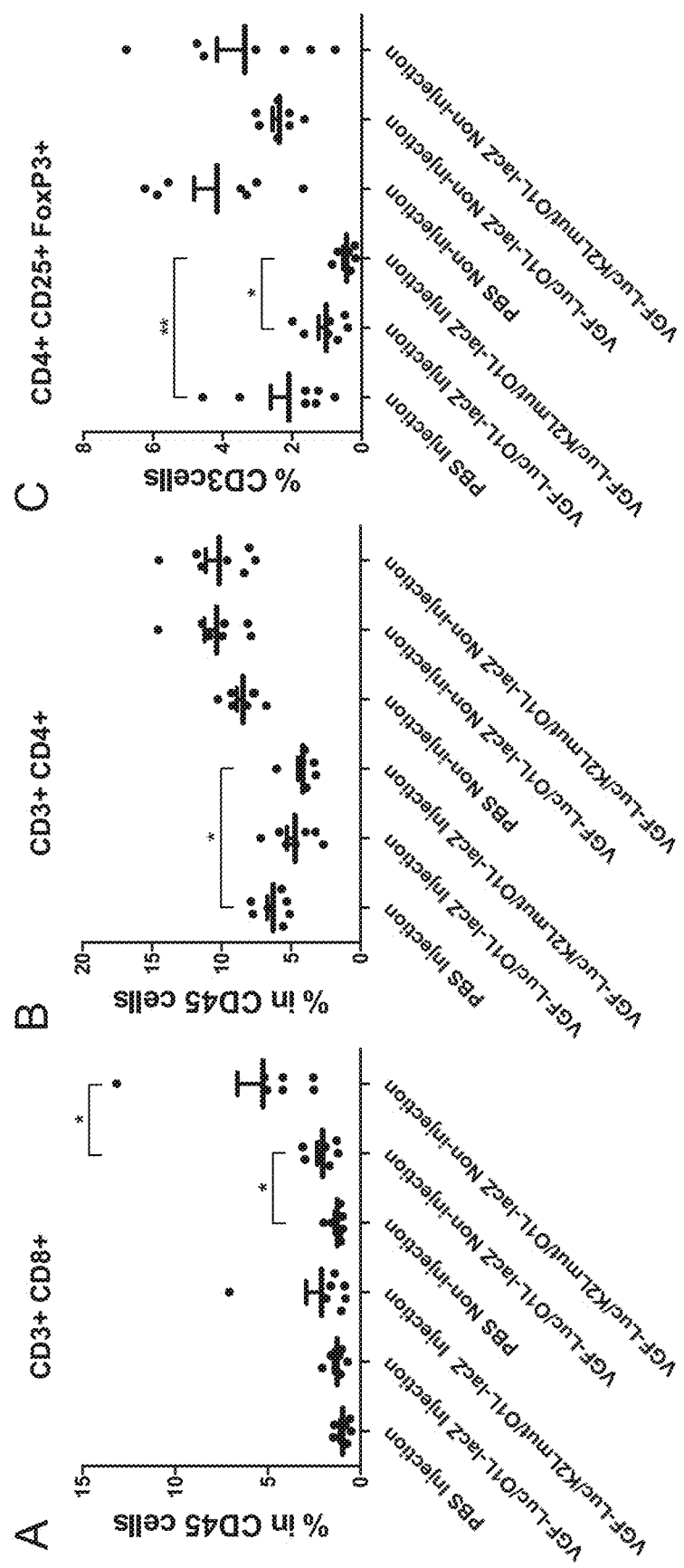
Figures 2, 10:
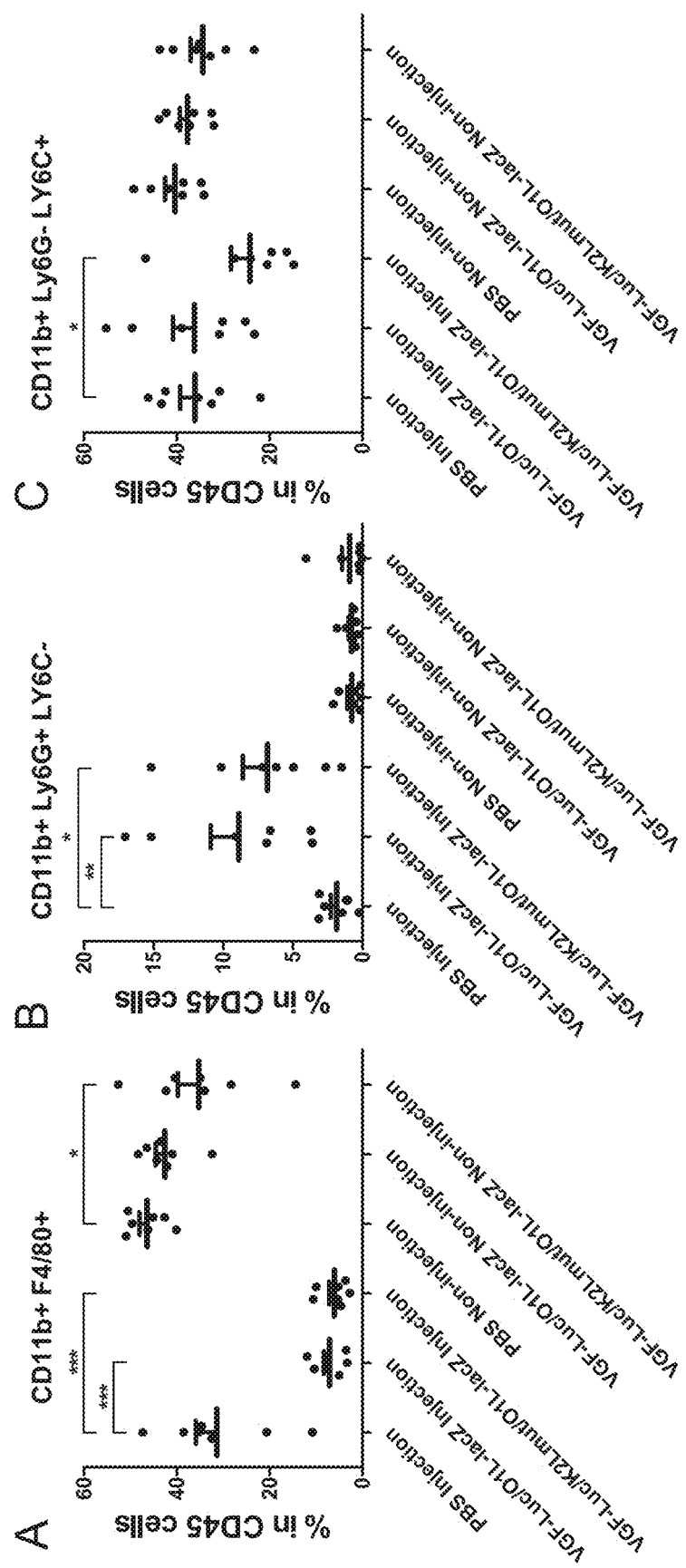

Analysis of Mechanisms of Therapeutic Effects of the Vaccinia Virus Having the Ability of Cell Fusion In Vivo In order to analyze the mechanism of improving therapeutic effects in vivo, subsequently, immunological analysis was performed by flow cytometry. Mouse colon cancer cells (CT26) were transplanted subcutaneously to both sides of the abdominal region of the BALB/cAjcl mice at $5.0 \times 10^5$ cells, and the tumors were allowed to grow to the volumes of 50 to 111 mm$^3$ (average: 60 mm$^3$) for 5 days. After the tumors had grown, VGF-Luc/O1L-LacZ and VGF-Luc/K2Lmut/O1L-LacZ were administered directly to the tumor on one side at $5.0 \times 10^7$ PFU every other day (3 instances in total) (Days 0, 2, and 4). The tumors on the both sides of the abdominal region were collected in serum free RPMI 5 days after virus administration (Day 5), and tumor tissue was dispersed using gentleMACS (Miltenyi Biotec). The cells were filtered through a 100-μm strainer, the resultant was subjected to hemolysis, the cells were counted, and the cell count was adjusted to $5.0 \times 10^5$ cells. The resulting cells were subjected to blocking with Fc block (BD Bioscience), cell surface antigen staining, and intracellular antigen staining, and CD8, CD4, Treg, TAM, and MDSC were analyzed by CytoFLEX (BECKMAN COULTER). Dead cell staining was carried out using 7AAD (BECKMAN COULTER), cell surface antigen staining was carried out using antibodies CD45 (30-F11; BioLegend), CD3 (145-2C11; BioLegend), CD8 (53-6.7; BioLegend), CD4 (GK1.5; Thermo), CD25 (PC61.5; Thermo), F4/80 (BM8; BioLegend), CD11b (M1/70; BioLegend), Ly6G (1A8; BioLegend), and Ly6C (AL21; BD Bioscience), and intracellular antigen staining was carried out using the FoxP3 antibody (FJK-16s; Thermo). FIG. 10-1 and FIG. 10-2 show the results of immune cell infiltration demonstrated as a result of immunological analysis. The level of CD8 T cell infiltration was likely to increase by VGF-Luc/K2Lmut/O1L-LacZ administration on the virus-administered side. As a result of the t-test, it was found to have increased to a significant extent, compared with VGF-Luc/O1L-LacZ administration, on the virus non-administered side ($*P=0.0413$). While the level of CD4 T cell infiltration had significantly decreased by VGF-Luc/K2Lmut/O1L-LacZ administration, compared with PBS administration, on the virus-administered side ($**P=0.0025$), it did not change on the virus non-administered side. While Treg had decreased as a result of VGF-Luc/K2Lmut/O1L-LacZ administration, compared with PBS administration, on the virus-administered side, no decrease was observed on the virus non-administered side ($*P=0.0362$, $**P=0.0094$). In addition, TAM had decreased as a result of VGF-luc/K2Lmut/O1L-LacZ administration, compared with PBS administration, both on the virus-administered side and on the virus non-administered side to a significant extent ($*P=0.0383$, $***P=0.0002$). In the end, G-MDSC of MDSC had increased to a significant extent as a result of virus administration on the virus-administered side ($*P=0.0179$, $**P=0.0051$). M-MDSC had decreased selectively as a result of VGF-Luc/K2Lmut/O1L-LacZ administration, compared with PBS administration, on the virus-administered side ($*P=0.0417$). This indicates that a decrease in immunosuppressive cells, such as Treg, TAM, and MDSC, and an increase in the level of CD8 T cell infiltration are critical for therapeutic effects on the virus-administered side and on the virus non-administered side, respectively.

Figure 11:
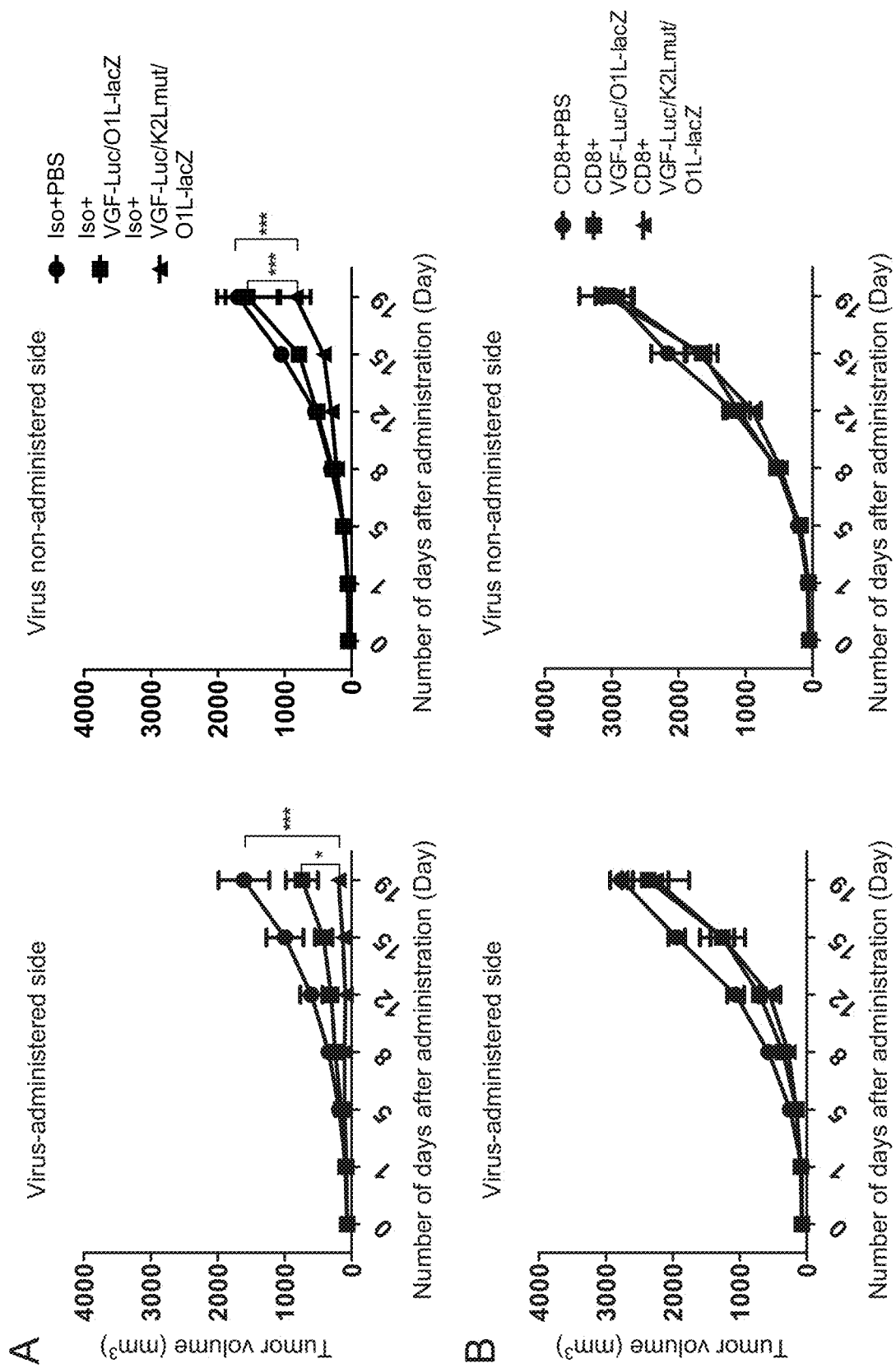
FIG. 11 shows the tumor volume in the allogeneic transplantation mouse models in which CD8 functions are suppressed after the therapy with the cell fusion-inducing gene recombinant vaccinia viruses.

The results of immunological analysis indicate that CD8 T cell infiltration is critical for therapeutic effects on the virus non-administered side. Accordingly, functions of CD8 T cells were suppressed by inhibitors. Mouse colon cancer cells (CT26) were transplanted subcutaneously to both sides of the abdominal region of the BALB/cAjcl mice at $5.0\times10^5$ cells, and the tumors were allowed to grow to the volumes of 42 to 128 mm³ (average: 60 mm³) for 5 days. After the tumors had grown, VGF-Luc/O1L-LacZ and VGF-Luc/K2Lmut/O1L-LacZ were administered directly to the tumor on one side at $5.0\times10^7$ PFU every other day (3 instances in total) (Days 0, 2, and 4). In addition, the InVivoPlus rat IgG2b isotype control, the anti-keyhole limpet hemocyanin clone LTF-2 (the isotype control), and the InVivoPlus anti-mouse CD8α Clone 2.43 (BioXCell) were administered intraperitoneally at 200 µg/mouse on Days −4, −2, 1, 3, 5, and 7. FIG. 11 shows the therapeutic effects examined by tumor volume measurement. FIG. 11A shows the results attained when the isotype control is administered and FIG. 11B shows the results attained when the anti-CD8 antibody is administered. When the isotype control is administered, as with the case shown in FIG. 9, tumor volumes were suppressed both on the virus-administered side and on the virus non-administered side of the mice to which VGF-Luc/O1L-LacZ had been administered and the mice to which VGF-Luc/K2Lmut/O1L-LacZ had been administered, compared with PBS mice. That is, significant differences were detected as a result of Two-Way ANOVA statistic analysis ($*P<0.05$, $***P<0.001$). When the anti-CD8 antibody was administered, some decrease was observed on the virus-administered side of the mice to which viruses had been administered, compared with PBS mice, and no differences were observed on the virus non-administered side of all mice. This indicates that CD8 T cell infiltration is critical not only on the virus non-administered side, but also on the virus-administered side.

Example 7

Therapeutic Effects of the Vaccinia Virus Having the Ability of Cell Fusion on Mouse Models Carrying Advanced Cancer The growth capacity and the transmissibility of viruses in vivo and the therapeutic effects of viruses when tumor volumes were further increased in mouse bodies were examined using allogeneic transplantation mouse models.

Figure 12:
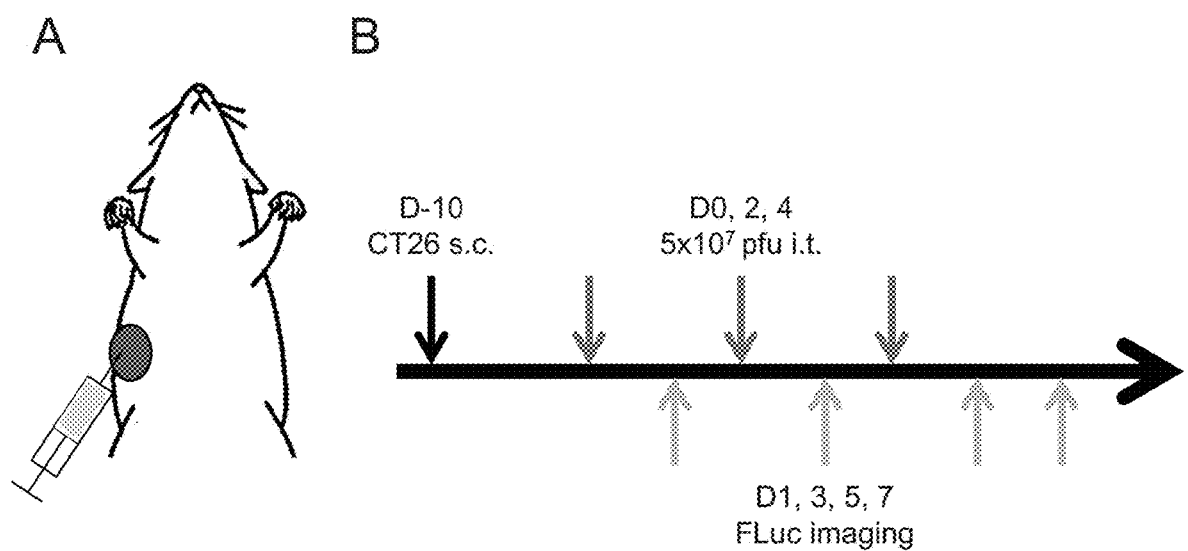
FIG. 12 shows an experimental system using allogeneic transplantation mouse models for advanced tumors.
Figures 2, 13:
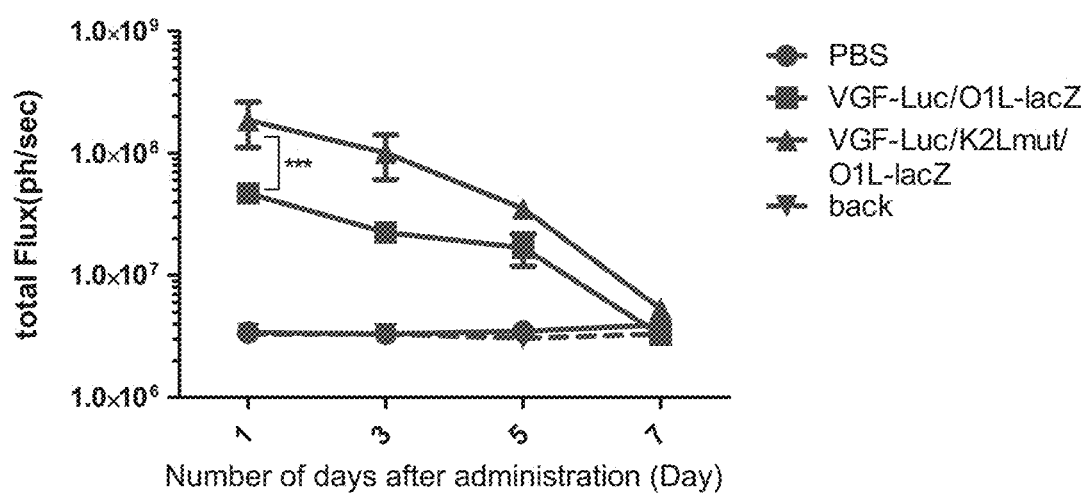
Figure 14:
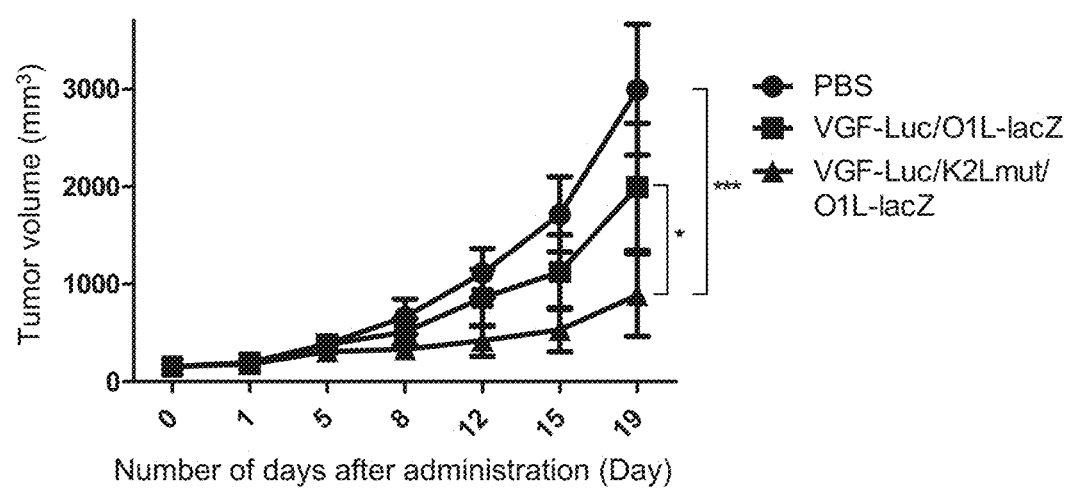
FIG. 14 shows the tumor volume in the allogeneic transplantation mouse models for advanced tumors after the therapy with the cell fusion-inducing gene recombinant vaccinia viruses.

Mouse colon cancer cells (CT26) were transplanted subcutaneously to one side of the abdominal region of the BALB/cAjcl mice at $5.0\times10^5$ cells, and the tumors were allowed to grow to the volumes of 87 to 253 mm³ (average: 150 mm³) for approximately 10 days (FIG. 12A). After the tumors had grown, VGF-Luc/O1L-LacZ and VGF-Luc/K2Lmut/O1L-LacZ were administered directly to the tumor at $5.0\times10^7$ PFU every other day (3 instances in total) (Days 0, 2, and 4). Also, FLuc luminescence of viruses (nearly equal to viral growth and transmission) was detected in a non-invasive manner by administering Vivo Glo Luciferin (Promega) and using the in vivo imaging system (Berthold, NightSHADE LB985) (Days 1, 3, 5, and 7) (FIG. 12B). FIG. 13-1 shows the results of detection of FLuc luminescence of viruses 1 day after virus administration. Concerning FLuc luminescence of viruses, VGF-Luc/K2Lmut/O1L-LacZ was observed to express signals at higher intensity, compared with VGF-Luc/O1L-LacZ, 1 day after virus administration (FIG. 13-1). When the FLuc expression levels were quantified, in addition, a significant difference was observed as a result of Two-Way ANOVA statistic analysis 1 day after virus administration (FIG. 13-2) ($***P<0.001$). Thus, it was demonstrated in vivo that the VGF-Luc/K2Lmut/O1L-LacZ viruses would actively grow and transmit. Thereafter, anti-cancer effects of viruses were examined by measuring tumor diameters. It was demonstrated as a result of Two-Way ANOVA statistic analysis that the tumor volume was suppressed to a significant extent in the mice to which VGF-Luc/K2Lmut/O1L-LacZ had been administered 19 days after virus administration, compared with the mice to which no viruses had been administered (PBS mice) and the mice to which VGF-Luc/O1L-LacZ had been administered ($*<0.05$, $***<0.001$) (FIG. 14).

Example 8

Anticancer Effects of the Vaccinia Viruses Having Both the Ability of Cell Fusion and the Tumor Targeting Ability In order to verify that anticancer effects resulting from cell fusion can be enhanced by application of, in addition to cell fusion, an extensive range of mutation, deletion, or insertion of a foreign gene to the K2L mutation, and in addition to tumor specificity attained by deletion of VGF and O1, a wide variety of methods in combination, an extensive range of vaccinia viruses having both the ability of cell fusion and the tumor targeting ability described below were prepared, and anticancer effects thereof in vitro were compared and evaluated.

Clones described below were used as the vaccinia viruses having both the ability of cell fusion and the tumor targeting ability.

VGF-LucGFP/ΔK2L-BFP/O1L-DsRed (FIG. 15-1A)
Clones deprived of K2L, having the ability of cell fusion, deprived of VGF and O1L, and maintaining tumor specificity
VGF-LucGFP (FIG. 15-1B)
Clones maintaining tumor specificity
TK-GFP (FIG. 15-1C)
Clones deprived of TK and thus maintaining tumor specificity
Unmodified virus (FIG. 15-1D)
Clones not deprived of any of K2L, VGF, O1L, and TK
VGF-LucGFP/K2L-BFP (FIG. 15-1E)
Clones deprived of K2L, having the ability of cell fusion, and deprived of VGF and thus maintaining tumor specificity
K2L-BFP/TK-GFP (FIG. 15-1F)
Clones deprived of K2L, having the ability of cell fusion, and deprived of TK and thus maintaining tumor specificity
K2L-BFP (FIG. 15-1G)
Clones deprived of K2L and having the ability of cell fusion Methods for producing such clones are described below.

Figures 1, 15:
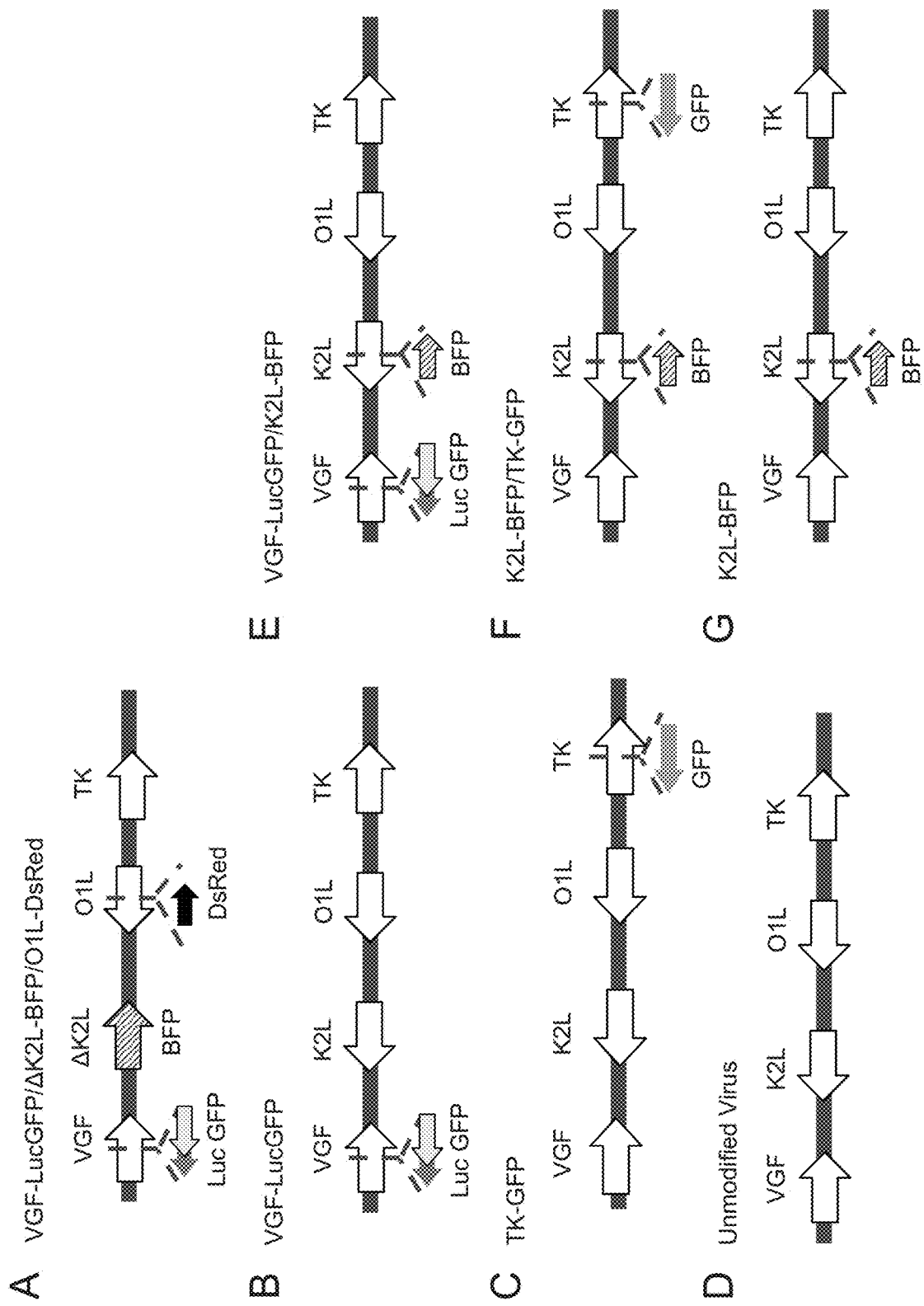
Figures 2, 15:
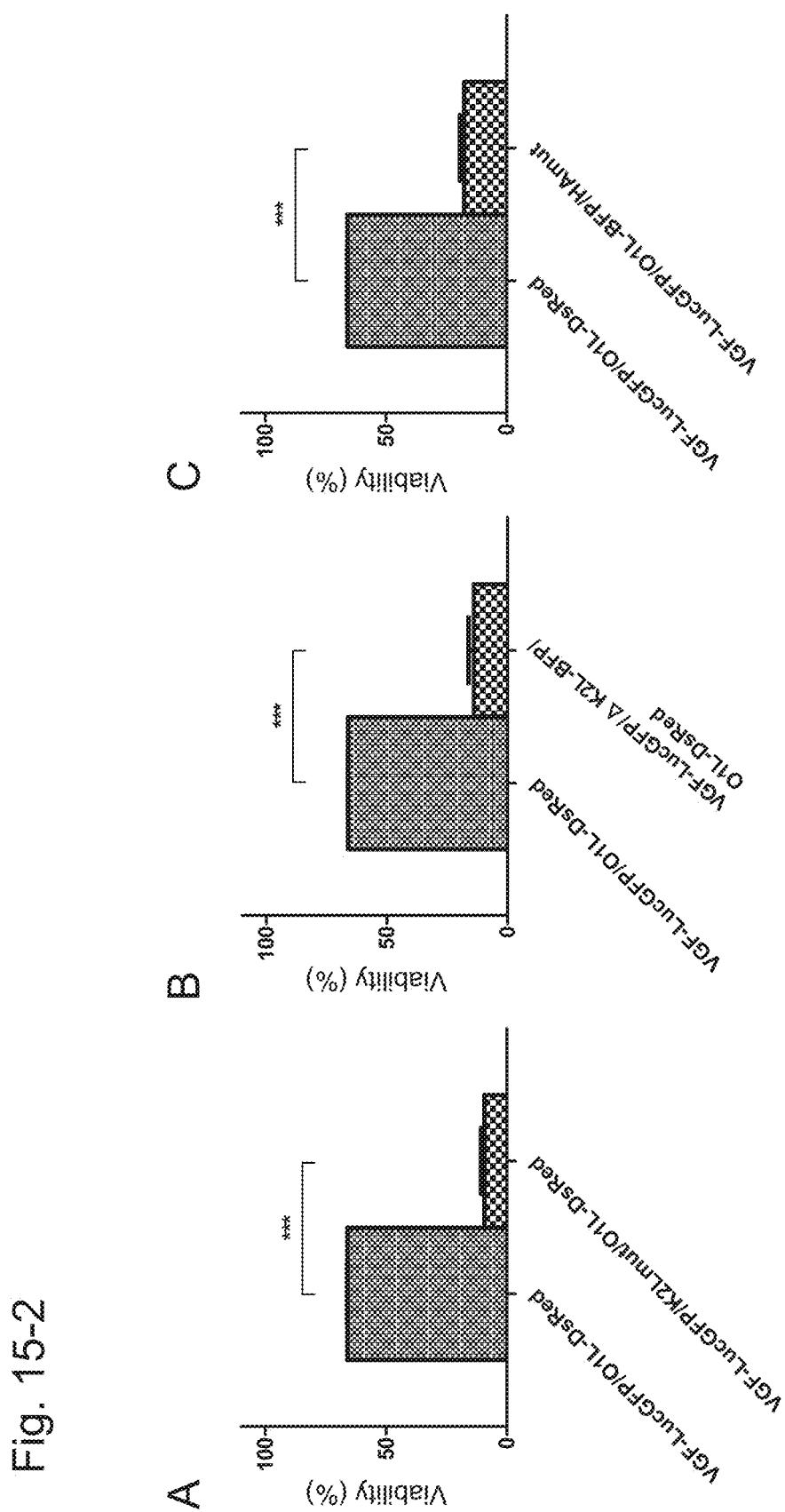
Figures 3, 15:
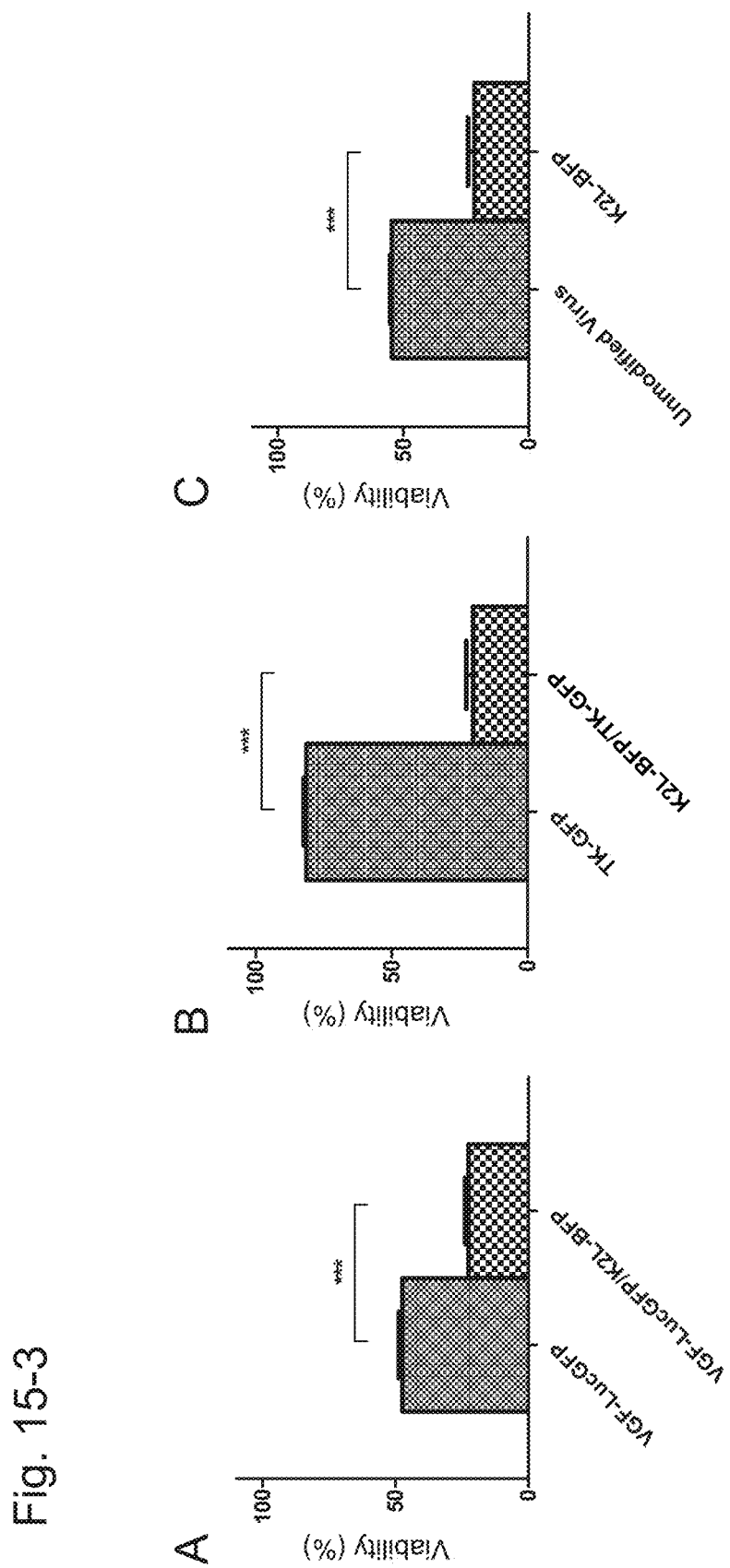
Figures 4, 15:
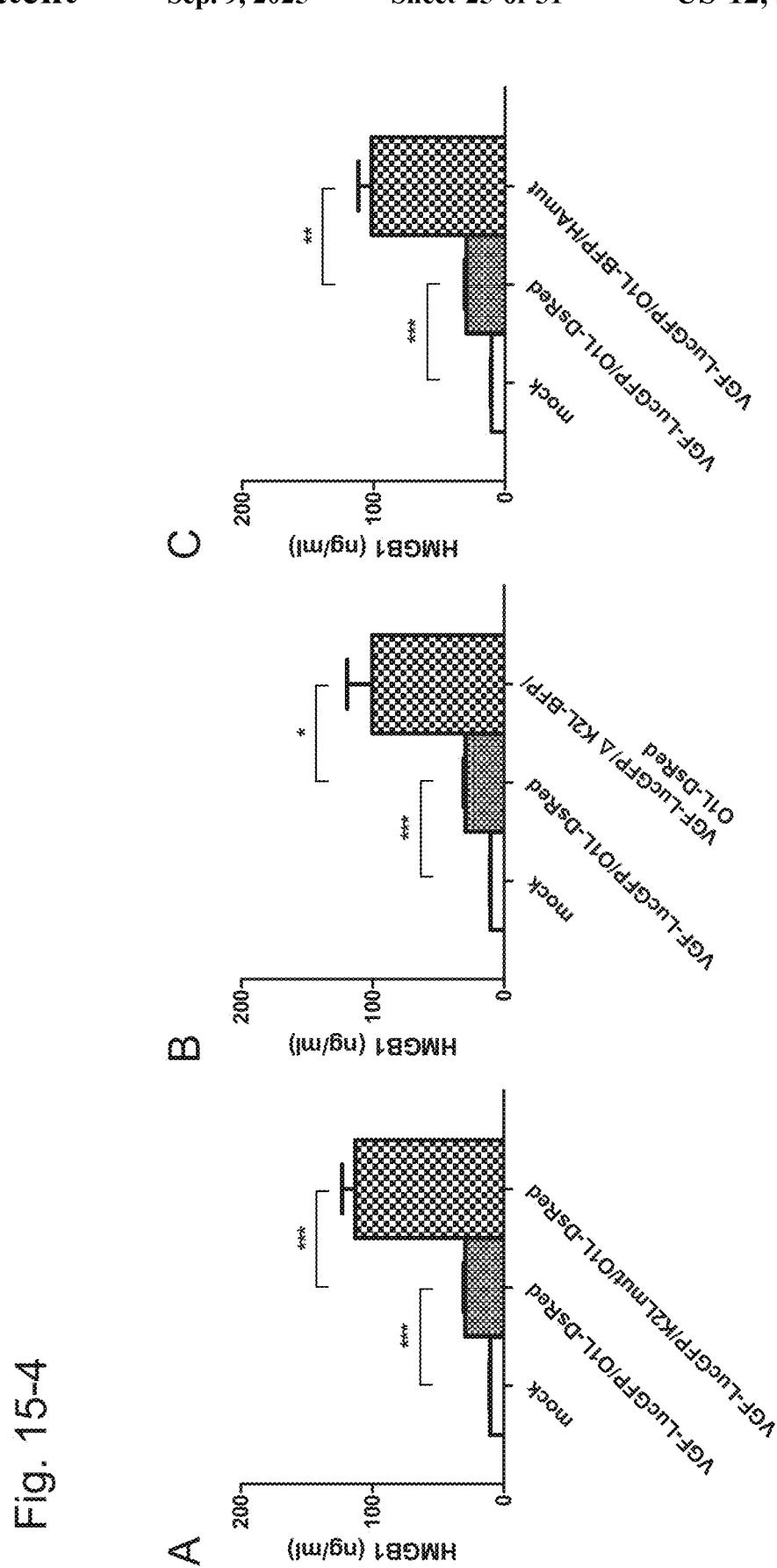
Figures 5, 15:
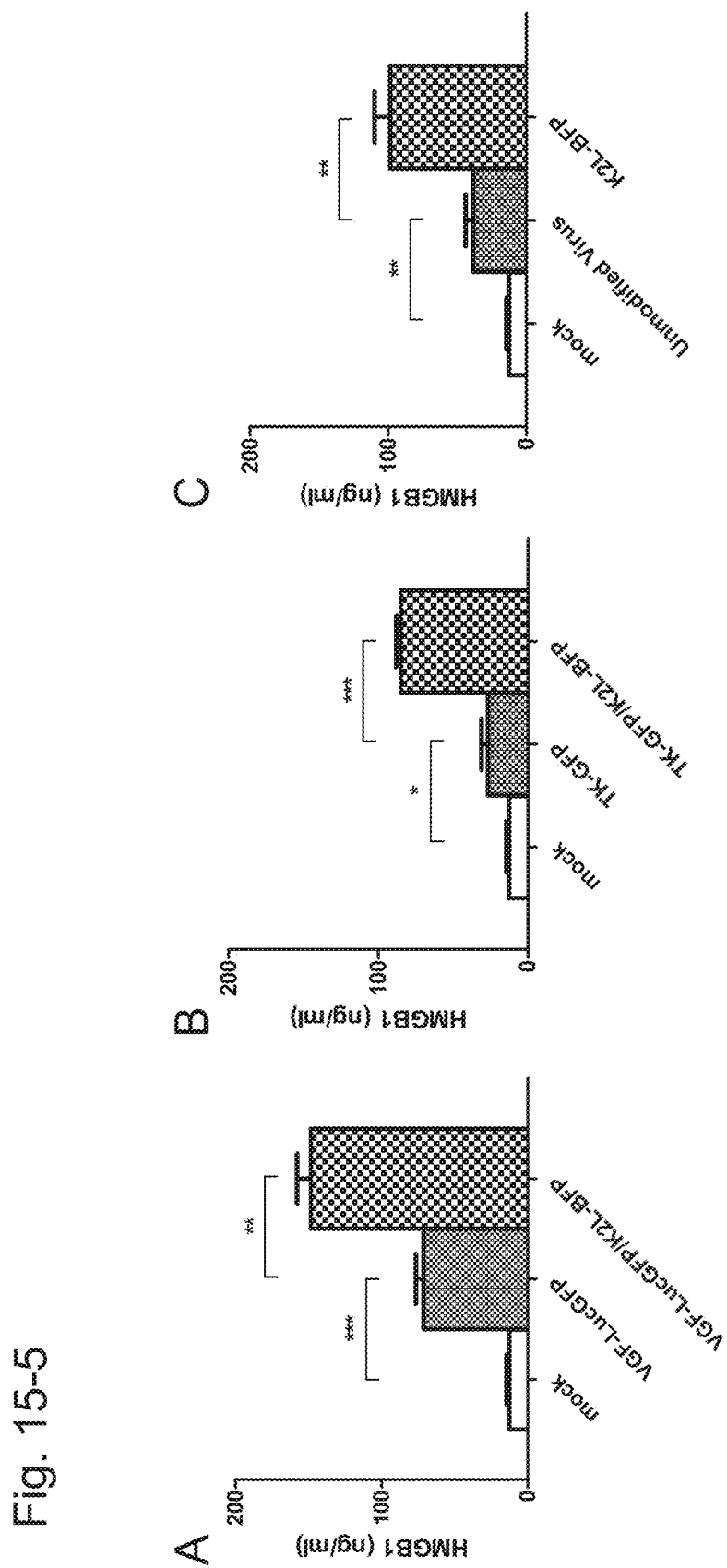

In order to prepare a gene recombinant vaccinia virus completely deprived of the K2L gene, the pTNshuttle/ΔK2L-BFP plasmid comprising a sequence (SEQ ID NO: 15) derived from a sequence comprising the K2L gene and the 5' and 3'-flanking regions thereof (SEQ ID NO: 14) by substitution of the K2L gene with the BFP gene was prepared. Based on the vaccinia virus (VGF-LucGFP/O1L-DsRed) and plasmid DNA of the transfer vector (pTNshuttle/ΔK2L-BFP), recombinant viruses were collected in the same manner as described above using BFP expression as the indicator and then subjected to screening by PCR. K2L was subjected to PCR with the use of the same primers as described above (SEQ ID NO: 12 and SEQ ID NO: 13), and clones in which PCR products of given sizes had been detected were examined in terms of their nucleotide sequences via direct sequencing and designated as VGF-LucGFP/ΔK2L-BFP/O1L-DsRed (FIG. 15-1A). In order to insert an expression unit of a different foreign gene into the K2L gene, the K2L gene region was amplified with the use of, as a template, genomic DNA of the LC16mO strain and two primers (SEQ ID NO: 16 and SEQ ID NO: 17). The PCR product was cleaved with the restriction enzymes XbaI and MfeI, and the cleavage product was cloned into the restriction enzyme sites XbaI and EcoRI of the pUC19 vector to construct pUC19-K2L. Subsequently, pTNshuttle/TK-SP-BFP was cleaved with the restriction enzymes SphI and EcoRI, the resultant was blunt-ended, the SP-BFP fragment was cloned into a site resulting from cleavage of the pUC19-K2L vector with the restriction enzyme ClaI and blunt-ending to construct pTNshuttle/K2L-SP-BFP. Based on the vaccinia virus (the unmodified virus strain without gene recombination; LC16mO strain) and plasmid DNA of the transfer vector (pTNshuttle/K2L-SP-BFP), recombinant viruses were collected in the same manner as described above using BFP expression as the indicator and then subjected to screening by PCR. K2L was subjected to PCR with the use of the same primers as described above (SEQ ID NO: 12 and SEQ ID NO: 13), and clones in which PCR products of given sizes had been detected were examined in terms of their nucleotide sequences via direct sequencing and designated as K2L-BFP (FIG. 15-1G). In order to insert an expression unit of a different foreign gene into the TK gene, pEGFP-N1 (Clontech Laboratories, Inc.) was cleaved with the restriction enzymes AgeI and NotI, the resultant was cloned into the same restriction enzyme site of the pTNshuttle/TK-SP-BFP vector to be substituted with the BFP gene, and pTNshuttle/TK-SP-GFP was thus constructed. Based on the vaccinia virus (the unmodified virus strain without gene recombination; LC16mO strain) and plasmid DNA of the transfer vector (pTNshuttle/TK-SP-GFP), recombinant viruses were collected in the same manner as described above using GFP expression as the indicator and then subjected to screening by PCR. TK was subjected to PCR with the use of two primers (SEQ ID NO: 18 and SEQ ID NO: 19), and clones in which PCR products of given sizes had been detected were examined in terms of their nucleotide sequences via direct sequencing and designated as TK-GFP (FIG. 15-1C). In order to prepare a vaccinia virus having both the ability of cell fusion and the tumor targeting ability, recombinant viruses were collected in the same manner as described above based on the VGF-deficient gene recombinant vaccinia virus strain (VGF-LucGFP, WO 2015/076422) or the TK-deficient gene recombinant vaccinia virus TK-GFP and plasmid DNA of the transfer vector (pTNshuttle/K2L-SP-BFP) and using BFP expression as the indicator, and the viruses were then subjected to screening by PCR. VGF was subjected to PCR with the use of the same primers as used above (SEQ ID NO: 10 and SEQ ID NO: 11), K2L was subjected to PCR with the use of the same primers as used above (SEQ ID NO: 12 and SEQ ID NO: 13), TK was subjected to PCR with the use of the same primers as used above (SEQ ID NO: 18 and SEQ ID NO: 19), and clones in which PCR products of given sizes had been detected were examined in terms of their nucleotide sequences via direct sequencing and designated as VGF-LucGFP/K2L-BFP (FIG. 15-1E) or K2L-BFP/TK-GFP (FIG. 15-1F). The recombinant viruses were mass-cultured in A549 cells, subjected to virus titer measurement in RK13 cells, and then subjected to experimentation.

Figure 5:
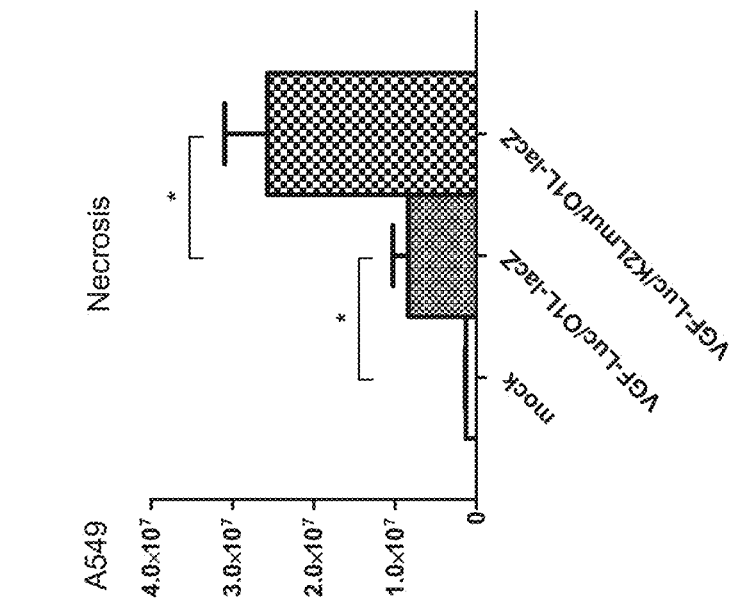
Figure 1:
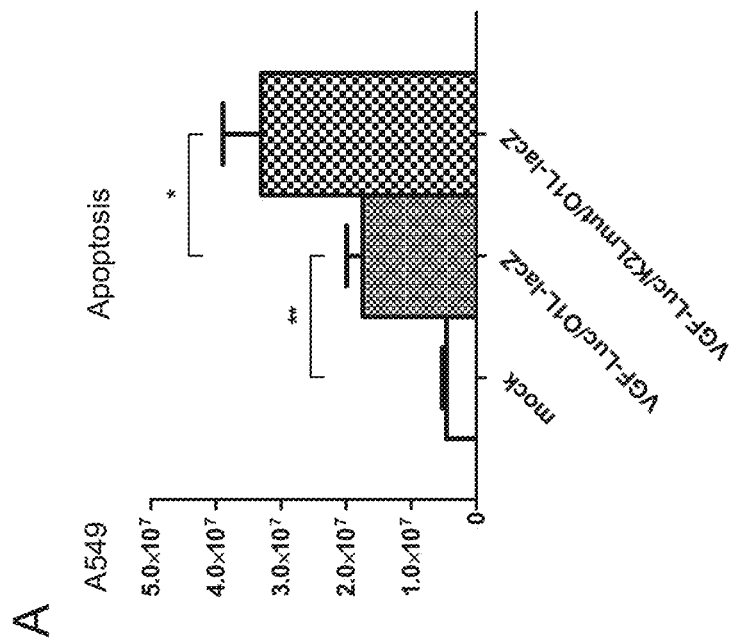
Figure 5:
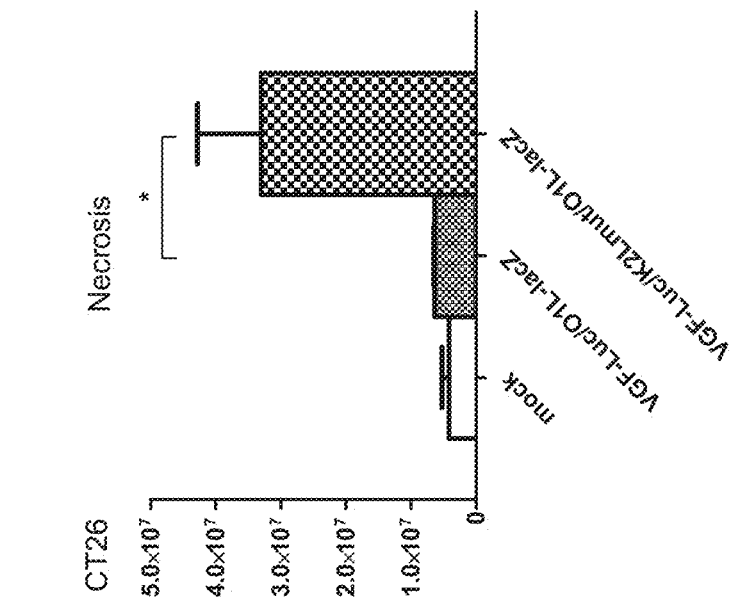
Figure 2:
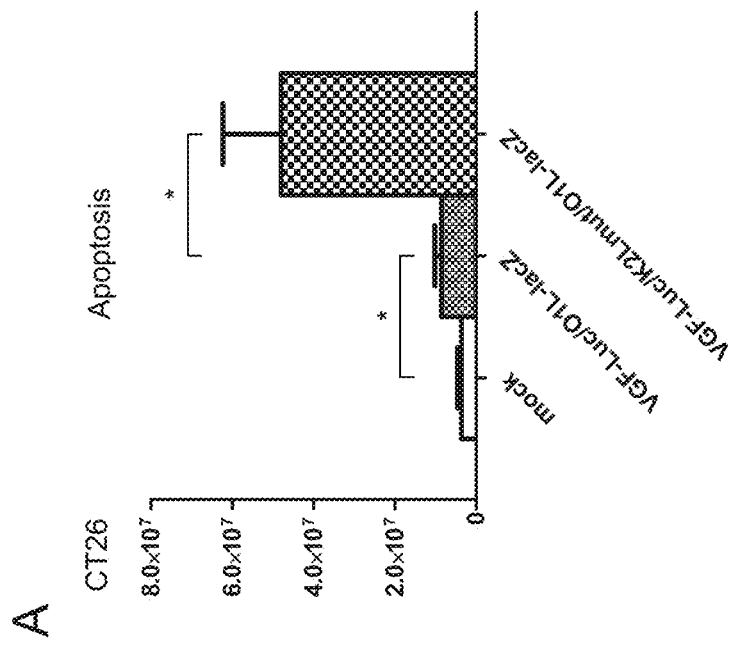

Subsequently, cell viability and ICD were examined in vitro. FIG. 15-2 and FIG. 15-3 show cell viability when infected with 10 types of viruses (VGF-LucGFP/O1L-DsRed (FIG. 1A), VGF-LucGFP/K2Lmut/O1L-DsRed (FIG. 1B), VGF-LucGFP/ΔK2L-BFP/O1L-DsRed (FIG. 15-1A), VGF-LucGFP/O1L-BFP/HAmut (FIG. 1C), VGF-LucGFP (FIG. 15-1B), VGF-LucGFP/K2L-BFP (FIG. 15-1E), TK-GFP (FIG. 15-1C), K2L-BFP/TK-GFP (FIG. 15-1F), unmodified virus (FIG. 15-1D), and K2L-BFP (FIG. 15-1G)). Human lung cancer cells (A549) were sowed at $1.0 \times 10^4$ cells/well on a 96-well plate, cultured at 37° C. for 24 hours, and then infected with the viruses having the structures shown in FIG. 1 and FIG. 15-1 at MOI of 0.1 (n=3). Cell viability was then measured by means of Cell-Titer 96® Aqueous Nonradioactive Cell Proliferation Assay (Promega) 72 hours after infection. As a result, cell viability was lowered by natural mutation of K2L, complete deprivation of K2L, and natural mutation of HA to a significant extent, compared with viruses without deprivation (VGF-LucGFP/O1L-Ds Red) (VGF-LucGFP/K2Lmut/O1L-DsRed, VGF-LucGFP/ΔK2L-BFP/O1L-DsRed, VGF-LucGFP/O1L-BFP/HAmut: *P<0.0001). This indicates that anticancer effects would be enhanced by cell fusion induced when K2L or HA becomes dysfunctional, regardless of the method of mutation or deletion. When K2L is inserted into or deleted from the VGF-deficient gene recombinant virus (VGF-LucGFP), the TK-deficient gene recombinant virus (TK-GFP), and a virus without tumor specificity (unmodified virus), cell viability was lowered to a significant extent (VGF-LucGFP/K2L-BFP, TK-GFP/K2L-BFP, K2L-BFP: *P≤0.0001). It was thus demonstrated that, upon cell fusion, anticancer effects would be enhanced, regardless of a type of tumor specificity and the presence or absence of tumor specificity. FIG. 15-4 and FIG. 15-5 show the results of ICD induction upon infection with the same 10 types of viruses as shown above. A549 cells were sowed at $5.25 \times 10^4$ cells/well on a 24-well plate, cultured at 37° C. for 24 hours, and then infected with the viruses having the structures shown in FIG. 1 and FIG. 15-1 at MOI of 1 (n=3). The culture supernatant was collected 60 hours after infection and quantified using the HMGB1 ELISA Kit II (Shino-Test Corporation). As a result, the extracellular release level of HMGB1 was increased by natural mutation of K2L, complete deprivation of K2L, and natural mutation of HA to a significant extent, compared with viruses without mutation or deprivation (VGF-LucGFP/O1L-DsRed) (VGF-LucGFP/K2Lmut/O1L-DsRed: ***P<0.0001; VGF-LucGFP/ΔK2L-BFP/O1L-DsRed: *P=0.0102; VGF-LucGFP/O1L-BFP/HAmut: P=0.0011). This indicates that the ability of ICD induction would be improved upon cell fusion when K2L or HA becomes dysfunctional, regardless of the method of mutation or deletion. When K2L is inserted into or deleted from the VGF-deficient gene recombinant virus (VGF-LucGFP), the TK-deficient gene recombinant virus (TK-GFP), and a virus without tumor specificity (unmodified virus), the extracellular release level of HMGB1 was increased to a significant extent (VGF-LucGFP/K2L-BFP: P=0.0010, TK-GFP/K2L-BFP: *P=0.0002, K2L-BFP: P=0.0042). It was thus demonstrated that, upon cell fusion, the ability of ICD induction would be improved, regardless of a type of tumor specificity and the presence or absence of tumor specificity.

Figure 16:
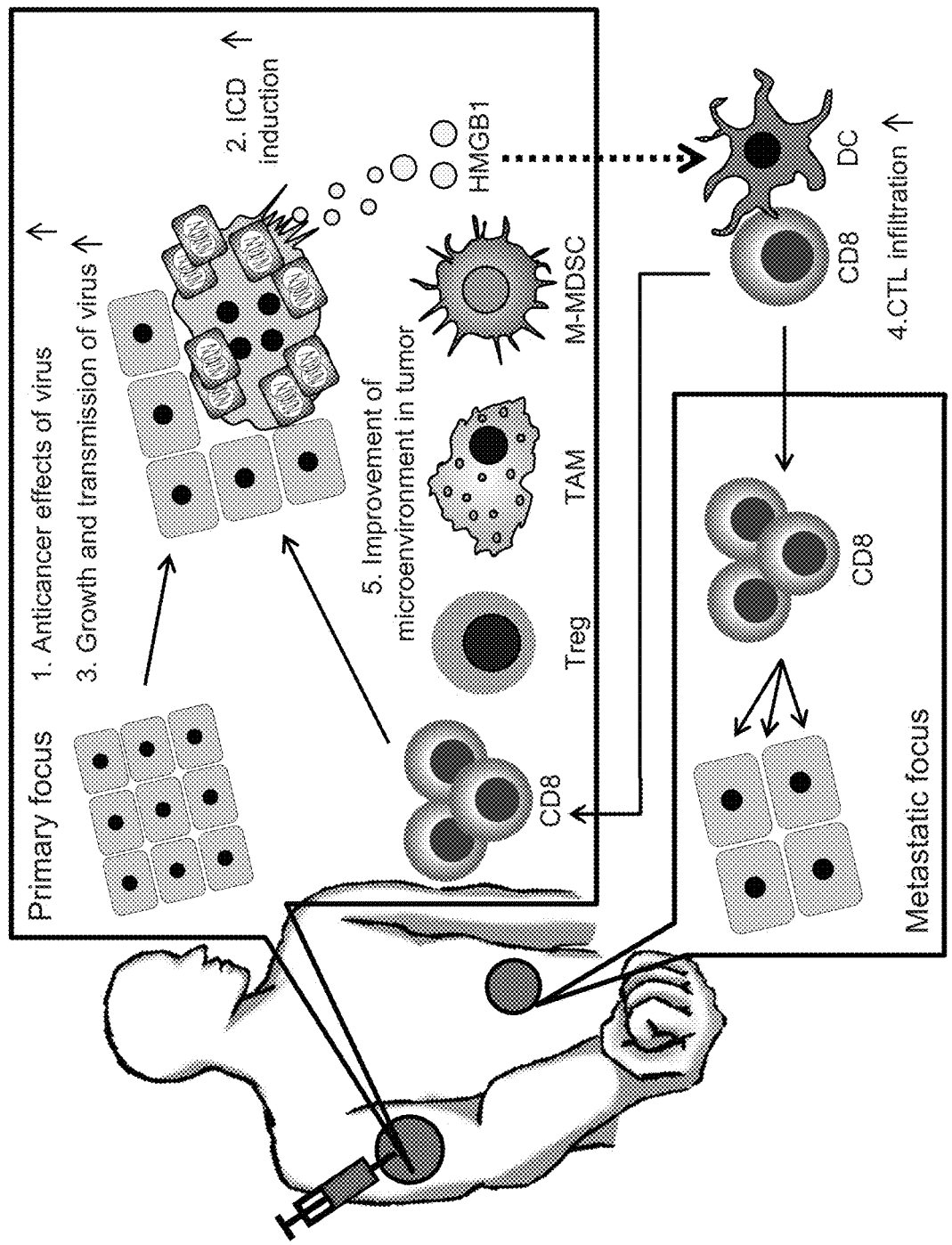
FIG. 16 summarizes a mechanism of improving anticancer effects by cell fusion-inducing oncolytic viruses.

The above results demonstrate that anticancer effects would be improved upon cell fusion induced by vaccinia viruses. As a result of analysis of the mechanism thereof, it was found that anticancer effects would be improved because of the 3 points described below. First of all, the growth capacity and the transmissibility of viruses are enhanced, oncolytic effects are improved, and apoptosis and necrosis then occur frequently. Subsequently, ICD is induced more efficiently as a result of cell fusion, and CD8 T cells frequently infiltrate the tumor on the virus-administered side and the tumor on the virus non-administered side. In the end, the immune environments of the tumor on the virus-administered side and the tumor on the virus non-administered side are improved, and anticancer immunity is then likely to function. Specifically, the cell fusion-inducing oncolytic viruses convert cold tumors that are less susceptible to the immune system to hot tumors that are prone to attack from the immune system, compared with oncolytic viruses that do not induce cell fusion, to exert higher anticancer effects than the oncolytic viruses that do not induce cell fusion (FIG. 16).

Example 9

Figure 17:
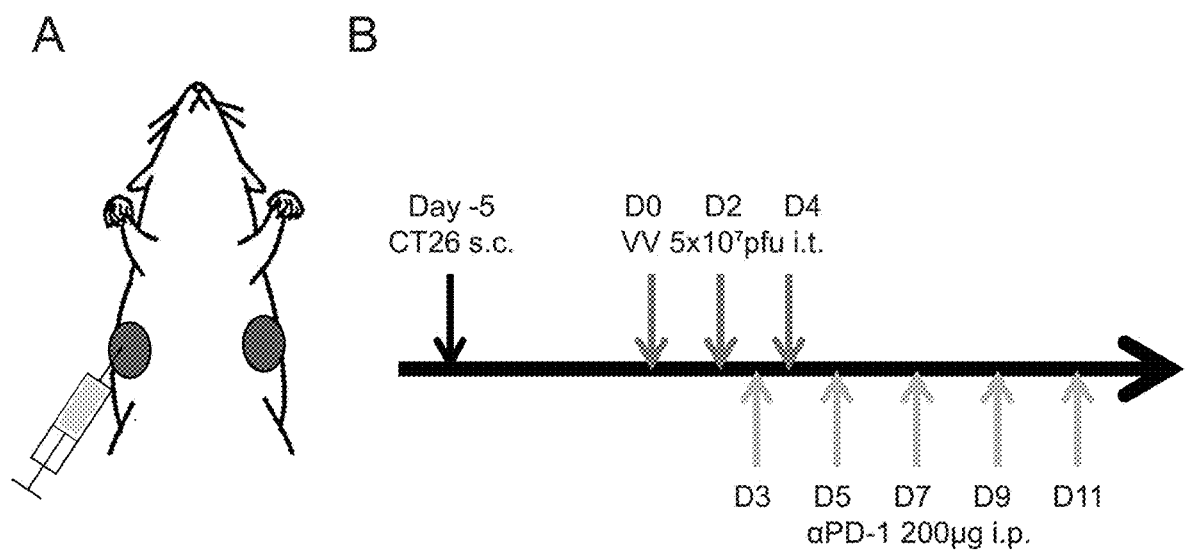
FIG. 17 shows an experimental system using the allogeneic transplantation mouse models in combination with the anti-PD-1 antibody.
Figure 18:
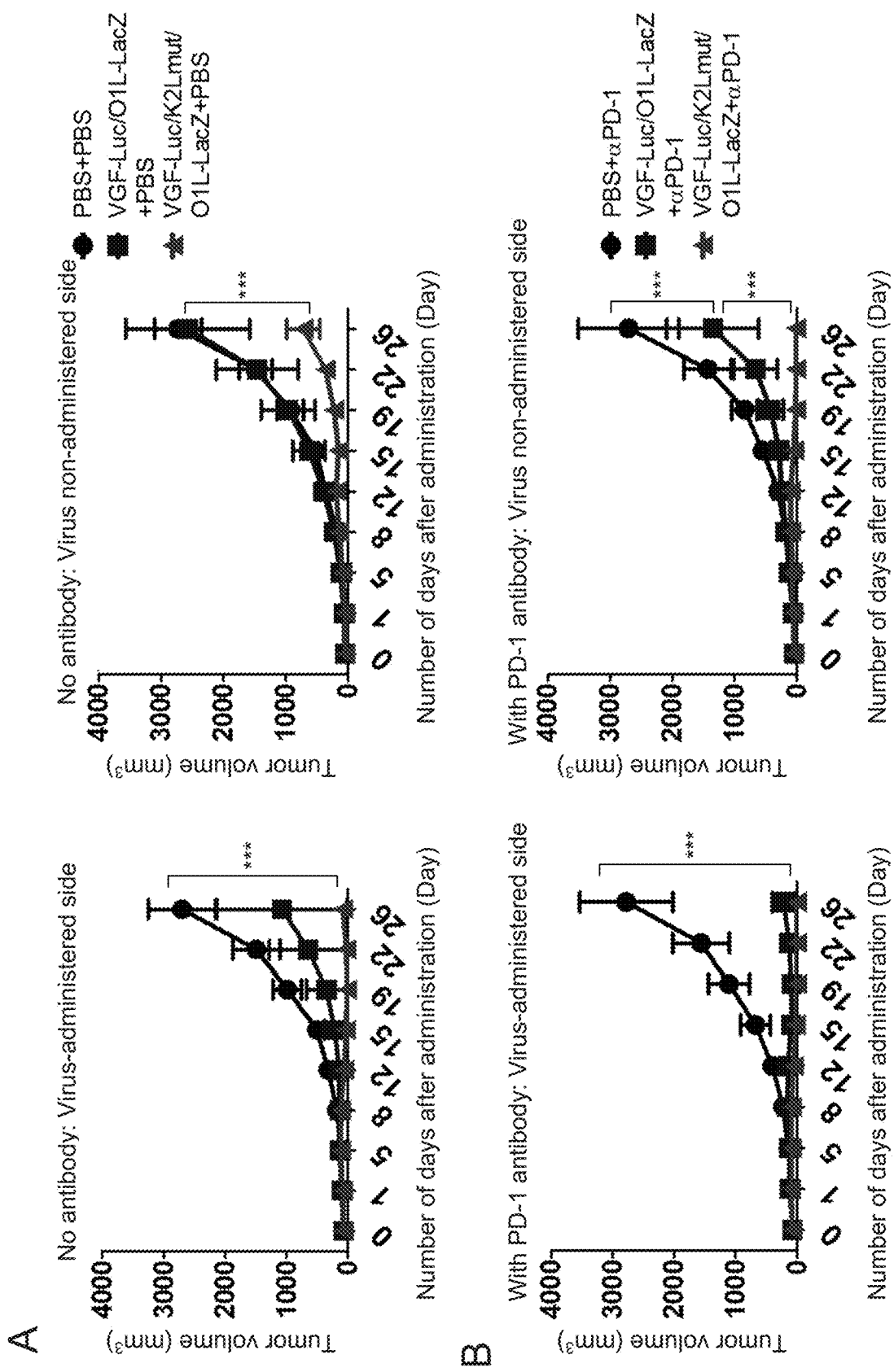
FIG. 18 shows the tumor volume in the allogeneic transplantation mouse models after the therapy with the cell fusion-inducing gene recombinant vaccinia viruses in combination with the anti-PD-1 antibody.

Therapeutic Effects Attained by the Vaccinia Virus Having the Ability of Cell Fusion in Combination With the Anti-PD-1 Antibody It was demonstrated that functions of CD8 T cells would be critical for therapeutic effects of viruses, in particular, therapeutic effects on the virus non-administered side. Thus, an immune checkpoint inhibitor; i.e., the anti-PD-1 antibody, was used in combination to promote functions of the CD8 T cells. Mouse colon cancer cells (CT26) were transplanted subcutaneously to both sides of the abdominal region of the BALB/cAjcl mice at $5.0 \times 10^5$ cells, and the tumors were allowed to grow to the volumes of 42 to 135 mm$^3$ (average: 70 mm$^3$) for 5 days. After the tumors had grown, VGF-Luc/O1L-LacZ and VGF-Luc/K2Lmut/O1L-LacZ were administered directly to the tumor on one side at $5.0 \times 10^7$ PFU every other day (3 instances in total) (Days 0, 2, and 4). In addition, PBS or InVivoPlus anti-mouse PD-1 Clone RMP1-14 (BioXCell) was administered intraperitoneally at 200 μg/mouse on Days 3, 5, 7, 9, and 11 (FIG. 17). In this case, the vaccinia viruses were administered, and the antibody was then administered on the following day. After the second vaccinia virus administration, the vaccinia virus and the antibody were alternately administered every day, virus administration was performed 3 times in total, and antibody administration was performed 5 times in total. FIG. 18 shows the results of examination of therapeutic effects by tumor volume measurement.

Figure 19:
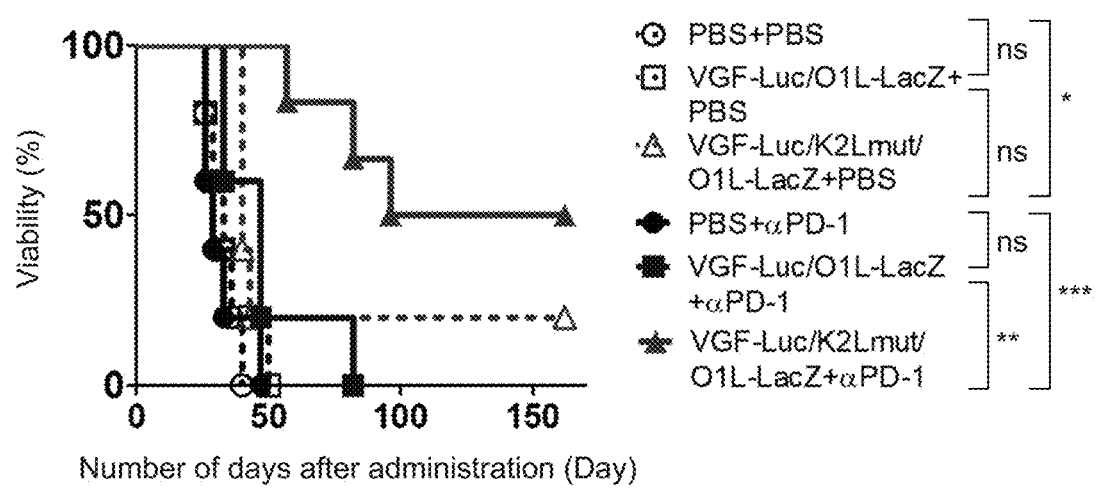
FIG. 19 shows the viability of the allogeneic transplantation mouse model after the therapy with the cell fusion-inducing gene recombinant vaccinia viruses in combination with the anti-PD-1 antibody.

When no antibody was administered, as with the case shown in FIG. 9, the tumor volume was suppressed on the virus-administered side of both of the mice to which VGF-Luc/O1L-LacZ had been administered and the mice to which VGF-Luc/K2Lmut/O1L-LacZ had been administered. Thus, a significant difference from the PBS mice was observed as a result of Two-Way ANOVA statistic analysis (*P<0.001). On the virus non-administered side, as with the case shown in FIG. 9, VGF-Luc/K2Lmut/O1L-LacZ administration exerted greater antitumor effects than those exerted by PBS or VGF-Luc/O1L-LacZ administration, although tumor remission was not achieved in substantially all mice. When the anti-PD-1 antibody was used in combination, tumor-suppressive effects were potentiated on the virus-administered side. Upon administration of VGF-Luc/O1L-LacZ, tumor remission was achieved in 3 out of 5 mice. Upon administration of VGF-Luc/K2Lmut/O1L-LacZ, tumor remission was achieved in all mice (6 out of 6 mice). When the anti-PD-1 antibody was used in combination, therapeutic effects of viruses were potentiated to a significant extent on the virus non-administered side. In the mice to which VGF-Luc/O1L-LacZ had been administered, however, tumor remission was not achieved on the virus non-administered side. As a result of Two-Way ANOVA statistic analysis, the tumor volume was suppressed in the mice to which VGF-Luc/K2Lmut/O1L-LacZ had been administered to a significant extent, compared with the mice to which VGF-Luc/O1L-LacZ had been administered (*<0.001), and tumor remission was achieved on both of the virus-administered side and the virus non-administered side of 3 out of 6 mice. FIG. 19 shows the survival curve of the mice after virus administration to which the anti-PD-1 antibody had been administered in combination. As a result of Log-rank statistic analysis, the survival period of the mice to which VGF-Luc/K2Lmut/O1L-LacZ had been administered was found to have been extended to a significant extent, compared with the mice to which PBS had been administered, when no antibody had been administered (*: P=0.0112); however, there was no significant difference from the mice to which VGF-Luc/O1L-LacZ had been administered. When the anti-PD-1 antibody was used in combination, in contrast, significant life-extending effects were observed in the mice to which VGF-Luc/K2Lmut/O1L-LacZ had been administered, compared with the mice to which PBS had been administered and the mice to which VGF-Luc/O1L-LacZ had been administered (*: P=0.0007, : P=0.0066).

Figure 20:
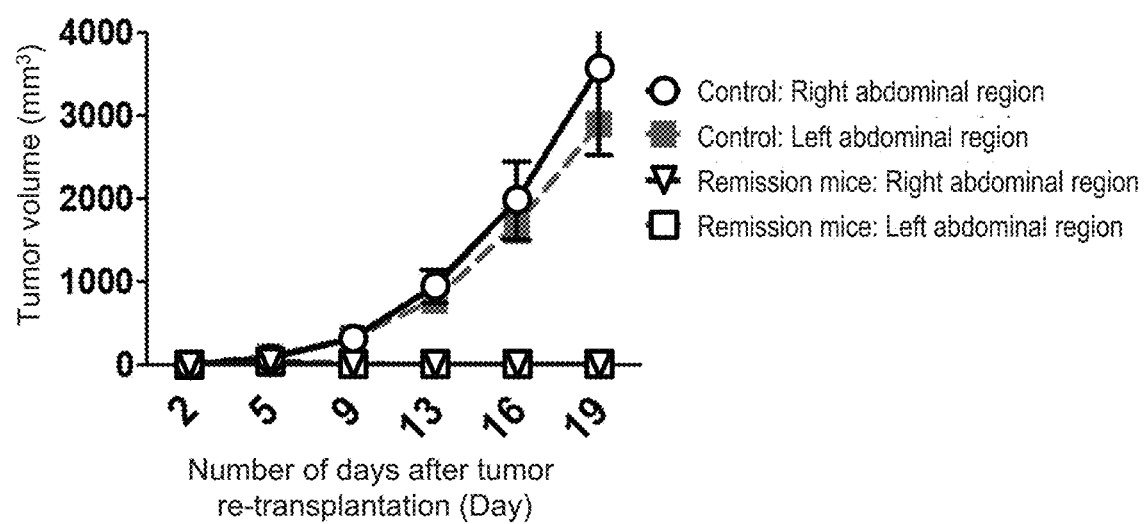
FIG. 20 shows the tumor volume after tumor re-transplantation to the mice that had achieved tumor remission by the therapy with the cell fusion-inducing gene recombinant vaccinia viruses in combination with the anti-PD-1 antibody.

In order to verify whether or not the mice that are completely cured of the tumor have the immunological memory against the tumor, subsequently, tumor cells were re-transplanted into the completely cured mice. To the mice that have achieved tumor remission as a result of administration of VGF-Luc/K2Lmut/O1L-LacZ in combination with the anti-PD-1 antibody, mouse colon cancer cells (CT26) were re-transplanted subcutaneously into the both sides of the abdominal region at $5.0 \times 10^5$ cells 101 days after virus administration. For comparison, tumor cells were transplanted hypodermically to naïve BALB/cAjcl mice at the same age in the same manner. FIG. 20 shows changes in tumor diameters after tumor re-transplantation. While the control mice exhibited tumor growth similar to that shown up to FIG. 9, no tumor growth was observed in the mice to which tumor cells had been re-transplanted after the tumors were completed cured.

As described above, use of the vaccinia virus having the ability of cell fusion in combination with the anti-PD-1 antibody would potentiate therapeutic effects of such vaccinia virus to a significant extent and would also promote induction of immunity against tumors and fixation of the immunological memory.

INDUSTRIAL APPLICABILITY

The vaccinia virus that induces cell fusion between infected cells can be used for cancer therapy.

All publications, patents, and patent applications cited herein are incorporated herein by reference in their entirety.

SEQUENCE LISTING FREE TEXT 1 to 4, 7, 8, 10 to 13, and 16 to 19: Primers

We claim:

1. An oncolytic vaccinia virus, which is deprived of functions of the K2L gene or the HA gene, or functions of the K2L gene and the HA gene, and further comprises deleting functions of the vaccinia virus growth factor (VGF) gene and O1L gene, and which has oncolytic effects of not growing in normal cells, growing specifically in cancer cells, specifically damaging cancer cells, induces cell fusion between infected cells, enhances a systemic anticancer immune activity, and induces cell death.

2. The oncolytic vaccinia virus according to claim 1, which enhances the ability of immunogenic cell death induction, increases the infiltration of CD8 T cells into cancer cells, and decreases immunosuppressive cells selected from Treg, TAM, or MDSC.

3. The oncolytic vaccinia virus according to claim 1, wherein the vaccinia virus is LC16 strain, LC16mO strain, or LC16m8 strain modified to express the B5R gene therein.

4. A pharmaceutical composition used for cancer therapy comprising the oncolytic vaccinia virus according to claim 3.

5. A vaccinia virus vector comprising foreign DNA introduced into the oncolytic vaccinia virus according to claim 3.

6. The vaccinia virus vector according to claim 5, wherein the foreign DNA is marker DNA, a therapeutic gene having cytotoxic or immunostimulatory effects, or DNA encoding an antigen of a cancer, a virus, a bacterium, or a protozoan.

7. A pharmaceutical composition used for cancer therapy or used as a vaccine against a cancer, a virus, a bacterium, or a protozoan, which comprises the vaccinia virus vector according to claim 5.

8. A method for producing an oncolytic vaccinia virus that has oncolytic effects of not growing in normal cells, growing specifically in cancer cells, specifically damaging cancer cells, induces cell fusion between infected cells, and enhances a systemic anticancer immune activity to induce cell death, comprising deleting functions of the K2L gene or the HA gene, or functions of the K2L gene and the HA gene from the vaccinia virus and further comprising deleting functions of the vaccinia virus growth factor (VGF) gene and O1L gene.

9. The method of production according to claim 8, wherein the vaccinia virus is LC16 strain, LC16mO strain, or LC16m8 strain modified to express the B5R gene therein.

10. A combination pharmaceutical kit used for cancer therapy, which comprises the oncolytic vaccinia virus according to claim 1 in combination with an immune checkpoint inhibitor.

11. The combination pharmaceutical kit according to claim 10, wherein the immune checkpoint inhibitor is anti-PD-1 antibody or anti-PD-L1 antibody.

12. The oncolytic vaccinia virus according to claim 1, which is used for cancer therapy in combination with the immune checkpoint inhibitor.

13. The oncolytic vaccinia virus according to claim 12, wherein the immune checkpoint inhibitor is anti-PD-1 antibody or anti-PD-L1 antibody.

* * * * *

UNITED STATES PATENT AND TRADEMARK OFFICE
CERTIFICATE OF CORRECTION

| | |
|---|---|
| PATENT NO. | : 12,409,198 B2 |
| APPLICATION NO. | : 17/610777 |
| DATED | : September 9, 2025 |
| INVENTOR(S) | : Takafumi Nakamura et al. |

Page 1 of 1

It is certified that error appears in the above-identified patent and that said Letters Patent is hereby corrected as shown below:

On the Title Page

Item (73) Assignee:
Assignee "Evolve Biotherapeutics Co., Ltd." is deleted.

Signed and Sealed this
Ninth Day of December, 2025

John A. Squires
*Director of the United States Patent and Trademark Office*